United States Patent
Daluge et al.

(10) Patent No.: US 7,115,590 B1
(45) Date of Patent: Oct. 3, 2006

(54) PHOSPHORAMIDATE, AND MONO-, DI-, AND TRI-PHOSPHATE ESTERS OF (1R, CIS)-4-(6-AMINO-9H-PURIN-9-YL)-2-CYCLOPENTENE-1-METHANOL AS ANTIVIRAL AGENTS

(75) Inventors: Susan Mary Daluge, Durham, NC (US); Christopher McGuigan, Whitechurch (GB)

(73) Assignee: University College Cardiff Consultants Limited, Cardiff (GB)

( * ) Notice: Subject to any disclaimer, the term of this patent is extended or adjusted under 35 U.S.C. 154(b) by 0 days.

(21) Appl. No.: 09/913,226

(22) PCT Filed: Feb. 10, 2000

(86) PCT No.: PCT/EP00/01045

§ 371 (c)(1),
(2), (4) Date: Oct. 26, 2001

(87) PCT Pub. No.: WO00/47591

PCT Pub. Date: Aug. 17, 2000

Related U.S. Application Data

(60) Provisional application No. 60/170,205, filed on Dec. 10, 1999.

(30) Foreign Application Priority Data

Feb. 12, 1999  (GB) .................. 9903090.0

(51) Int. Cl.
- *C07F 9/6561* (2006.01)
- *A61K 31/675* (2006.01)
- *A61P 31/18* (2006.01)
- *A61P 31/20* (2006.01)

(52) U.S. Cl. ......................... 514/81; 544/244

(58) Field of Classification Search ................ 544/244; 514/81

See application file for complete search history.

(56) References Cited

U.S. PATENT DOCUMENTS

| | | | | |
|---|---|---|---|---|
| 5,244,896 | A * | 9/1993 | Borcherding et al. | 514/261.1 |
| 6,455,513 | B1 * | 9/2002 | McGuigan et al. | 514/81 |
| 6,638,919 | B1 * | 10/2003 | McGuigan et al. | 514/81 |
| 6,828,319 | B1 * | 12/2004 | Jagtap et al. | 514/232.8 |
| 6,887,707 | B1 * | 5/2005 | Loeb et al. | 435/442 |
| 2003/0045508 | A1 * | 3/2003 | Daluge et al. | 544/244 |

OTHER PUBLICATIONS

Kim, J. Med Chem 33, 1207 (1990).*
Semizarov et al.: "Selectivity of DNA Polymerases toward alpha and beta Nucleotide Substrates of D and L series" FEBS LETT., vol. 354, No. 2, Nov. 7, 1994, pp. 187-190.
Faletto et al.: "Unique Intracellular Activation of the Potent Anti-Human Immundeficiency Virus Agent 1592U89" Antimicrobial Agents and Chemotherapy, vol. 41, No. 5, May 1997, pp. 1099-1107.

* cited by examiner

*Primary Examiner*—Mark L. Berch
(74) *Attorney, Agent, or Firm*—Mathews, Shepherd, McKay & Bruneau, P.A.

(57) ABSTRACT

The present invention relates to phosphoramidate, and phosphate esters of (1R,cis)-4-(6-amino-9H-purin-9-yl)-2-cyclopentene-1nethanol, processes for their preparation, and their use in treating viral infections.

26 Claims, No Drawings

PHOSPHORAMIDATE, AND MONO-, DI-, AND TRI-PHOSPHATE ESTERS OF (1R, CIS)-4-(6-AMINO-9H-PURIN-9-YL)-2-CYCLOPENTENE-1-METHANOL AS ANTIVIRAL AGENTS

This application is filed pursuant to 35 U.S.C. §371 as a United States National Phase Application of International Application No. PCT/EP00/01045 filed Feb. 10, 2000 which claims priority from GB9903090.0 filed Feb. 12, 1999 in the United Kingdom and 60/170,205 filed Dec. 10, 1999 in the United States

FIELD OF THE INVENTION

The present invention relates to certain analogs of (1R,cis)-4-(6-amino-9H-purin-9-yl)-2-cyclopentene-1-methanol and their use in medical therapy.

BACKGROUND OF THE INVENTION

Retroviruses form a sub-group of RNA viruses which, in order to replicate, must first "reverse transcribe" the RNA of their genome into DNA ("transcription" conventionally describes the synthesis of RNA from DNA). Once in the form of DNA, the viral genome may be incorporated into the host cell genome, allowing it to take advantage of the host cell's transcription/translation machinery for the purposes of replication. Once incorporated, the viral DNA is virtually indistinguishable from the host's DNA and, in this state, the virus may persist for the life of the cell.

A species of retrovirus, the Human immunodeficiency virus (HIV) has been reproducibly isolated from patients with AIDS (acquired immunodeficiency syndrome) or with the symptoms that frequently precede AIDS. AIDS is an immunosuppressive or immunodestructive disease that predisposes subjects to fatal opportunistic infections. Characteristically, AIDS is associated with a progressive depletion of T-cells, especially the helper-inducer subset bearing the CD4 surface marker. HIV is cytopathic and appears to preferentially infect and destroy T-cells bearing the CD4 marker, and it is now generally recognized that HIV is the etiological agent of AIDS. Clinical conditions such as AIDS-related complex (ARC), progressive generalized lymphadenopathy (PGL), Kaposi's sarcoma, thrombocytopenic purpura, AIDS-related neurological conditions, such as AIDS dementia complex, multiple sclerosis or tropical paraparesis, and also anti-HIV antibody-positive and HIV-positive conditions, including such conditions in asymptomatic patients, are also conditions which may be treated by appropriate anti-viral therapy.

Another RNA virus which has been recognized as the causative agent of an increasingly serious international health problem is the non-A, non-B hepatitis virus. At least 80% of cases of chronic post-transfusional non-A, non-B hepatitis have been shown to be due to the virus now identified as hepatitis C and this virus probably accounts for virtually all cases of post-transfusional hepatitis in clinical settings where blood products are screened for hepatitis B. Whereas approximately half of the cases of acute hepatitis C infection resolve spontaneously over a period of months, the remainder become chronic and in many if not all such cases chronic active hepatitis ensues with the potential for cirrhosis and hepatocellular carcinoma. The structure of the hepatitis C virus genome has been elucidated and the virus has been characterized as a single stranded RNA virus with similarities to flaviviruses.

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck. Recent insights into the mechanism of replication of the hepadnavirus genome indicate the importance of reverse transcription of an RNA intermediate, suggesting that the reverse transcriptase is a logical chemotherapeutic target. HBV is a viral pathogen of major worldwide importance. The virus is etiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

U.S. Pat. No. 4,916,224 discloses 2',3'-dideoxy-2',3'-didehydro-carbocyclic nucleosides and their use in the treatment of HIV. WO 96/29336 discloses masked monophosphate nucleoside analogues for the treatment of HIV. Wang et al. (*Bioorganic Et Medicinal Chemistry Letters* 8, pp. 1585–1588, 1998) disclose the synthesis of L-carbocyclic 2',3'-didehydro-2',3'-dideoxyadensosine and its use in HIV infections.

It has now been discovered that certain phosphoramidates of (1R,cis)-4-(6-amino-9H-purin-9-yl)-2-cyclopentene-1-methanol are useful for the treatment of viral infections, particularly hepatitis B and retroviral infections, especially HIV. Compounds of the present invention have pharmacokinetic properties which render them advantageous as therapeutic agents.

SUMMARY OF THE INVENTION

The present invention relates to compounds of formula (I)

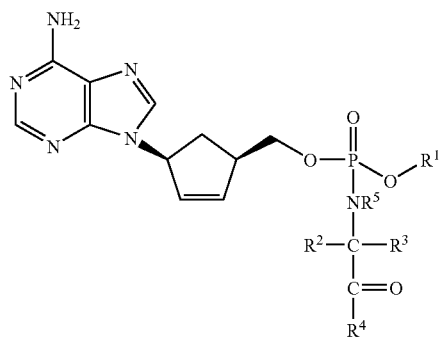

wherein:

$R^1$ is hydrogen; $C_{6-14}$ aryl; or heteroaryl, optionally substituted with one or more substituents selected from the group consisting of $C_{1-6}$alkoxy, nitro, halogen, amino, hydroxy, carboxylate and esters thereof, carboxyalkyl, —CONHR$^6$, and —CONR$^6$R$^7$, wherein R$^6$ and R$^7$, which may be the same or different, are independently selected from $C_{1-8}$alkyl, $C_{1-8}$alkylaryl or $C_{6-14}$aryl;

$R^2$ and $R^3$ are independently selected from hydrogen or $C_{1-8}$alkyl, $C_{3-8}$cycloalkyl, $C_{2-8}$alkenyl, $C_{5-8}$cycloalkenyl, $C_{6-14}$aryl, or aralkyl wherein each $C_{1-8}$alkyl, $C_{3-8}$cycloalkyl, $C_{2-8}$alkenyl, $C_{5-8}$cycloalkenyl, $C_{6-14}$aryl or aralkyl may be optionally substituted with one or more substituents selected from the group consisting of $C_{1-8}$alkyl, halo, hydroxy, alkoxy, amino, aminoalkyl, aminodialkyl, —SH, thioalkyl, heterocycle, carboxylate and esters thereof, carboxyalkyl, —CONHR$^6$, and —CONR$^6$R$^7$, wherein $R^6$ and $R^7$, which may be the same or different, are independently selected from $C_{1-8}$alkyl, $C_{1-8}$alkylaryl or $C_{6-14}$aryl; or $R^2$ and $R^3$ can together form a 3 to 8-membered ring;

$R^4$ is —OR$^8$, —NR$^8$R$^9$ or —SR$^8$, where $R^8$ and $R^9$, which may be the same or different, are independently selected from hydrogen; or $C_{1-8}$alkyl, $C_{3-8}$cycloalkyl, $C_{2-8}$alkenyl, $C_{5-8}$cycloalkenyl, aralkyl, heteroaryl, or $C_{6-14}$aryl wherein each $C_{1-8}$alkyl, $C_{3-8}$cycloalkyl, $C_{2-8}$alkenyl, $C_{5-8}$cycloalkenyl, aralkyl, heteroaryl, or $C_{6-14}$aryl may be optionally substituted with one or more substituents selected from the group consisting of halo, hydroxy, alkoxy, amino, aminoalkyl, aminodialkyl, —SH, thioalkyl, carboxylate and esters thereof, carboxyalkyl, —CONHR$^6$, and —CONR$^6$R$^7$, wherein $R^6$ and $R^7$, which may be the same or different, are independently selected from $C_{1-8}$alkyl, $C_{1-8}$alkylaryl or $C_{6-14}$aryl;

$R^5$ is hydrogen; $C_{1-8}$alkyl; or $C_{6-14}$aryl; or $R^2$ and $R^5$ may together form a 5- or 6-membered ring or $R^3$ and $R^5$ may together form a 5- or 6-membered ring;

or a pharmaceutically acceptable derivative thereof, and their use in the treatment of viral infections.

DETAILED DESCRIPTION OF THE INVENTION

The present invention features compounds of formula (I)

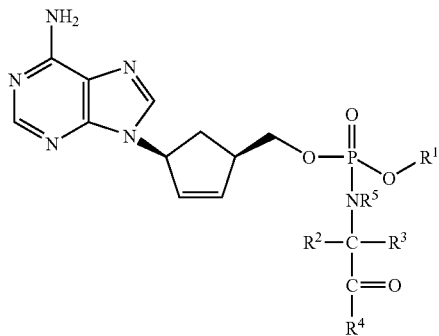

wherein:

$R^1$ is hydrogen; $C_{6-14}$aryl; or heteroaryl, optionally substituted with one or more substituents selected from the group consisting of $C_{1-6}$alkoxy, nitro, halogen, amino, hydroxy, carboxylate and esters thereof, carboxyalkyl, —CONHR$^6$, and —CONR$^6$R$^7$, wherein $R^6$ and $R^7$, which may be the same or different, are independently selected from $C_{1-8}$alkyl, $C_{1-8}$alkylaryl or $C_{6-14}$aryl;

$R^2$ and $R^3$ are independently selected from hydrogen or $C_{1-8}$alkyl, $C_{3-8}$cycloalkyl, $C_{2-8}$alkenyl, $C_{5-8}$cycloalkenyl, $C_{6-14}$aryl, or aralkyl wherein each $C_{1-8}$alkyl, $C_{3-8}$cycloalkyl, $C_{2-8}$alkenyl, $C_{5-8}$cycloalkenyl, $C_{6-14}$aryl or aralkyl may be optionally substituted with one or more substituents selected from the group consisting of $C_{1-8}$alkyl, halo, hydroxy, alkoxy, amino, aminoalkyl, aminodialkyl, —SH, thioalkyl, heterocycle, carboxylate and esters thereof, carboxyalkyl, —CONHR$^6$, and —CONR$^6$R$^7$, wherein $R^6$ and $R^7$, which may be the same or different, are independently selected from $C_{1-8}$alkyl, $C_{1-8}$alkylaryl or $C_{6-14}$aryl; or $R^2$ and $R^3$ can together form a 3 to 8-membered ring;

$R^4$ is —OR$^8$, —NR$^8$R$^9$ or —SR$^8$, where $R^8$ and $R^9$, which may be the same or different, are independently selected from hydrogen; or $C_{1-8}$alkyl, $C_{3-8}$cycloalkyl, $C_{2-8}$alkenyl, $C_{2-8}$cycloalkenyl, aralkyl, heteroaryl, or $C_{6-14}$aryl wherein each $C_{1-8}$alkyl, $C_{3-8}$cycloalkyl, $C_{2-8}$alkenyl, $C_{5-8}$cycloalkenyl, aralkyl, heteroaryl, or $C_{6-14}$aryl may be optionally substituted with one or more substituents selected from the group consisting of halo, hydroxy, alkoxy, amino, aminoalkyl, aminodialkyl, —SH, thioalkyl, carboxylate and esters thereof, carboxyalkyl, —CONHR$^6$, and —CONR$^6$R$^7$, wherein $R^6$ and $R^7$, which may be the same or different, are independently selected from $C_{1-8}$alkyl, $C_{1-8}$alkylaryl or $C_{6-14}$aryl;

$R^5$ is hydrogen; $C_{1-8}$alkyl; or $C_{6-14}$aryl; or $R^2$ and $R^5$ may together form a 5- or 6-membered ring or $R^3$ and $R^5$ may together form a 5- or 6-membered ring;

or a pharmaceutically acceptable derivative thereof, and their use in the treatment of viral infections.

An embodiment of the present invention features compounds of formula (II)

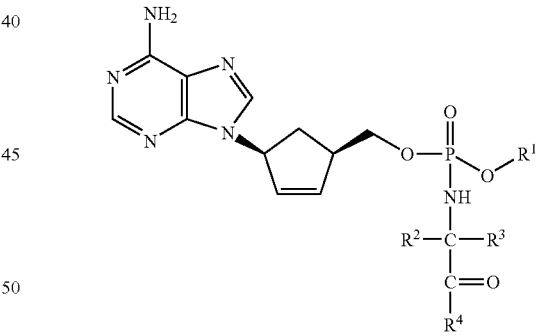

wherein:

$R^1$ is hydrogen; $C_{6-14}$aryl; or heteroaryl, optionally substituted with one or more substituents selected from $C_{1-6}$alkoxy, nitro, halogen, amino, carboxylate and hydroxy.

$R^2$ and $R^3$ are independently selected from hydrogen, $C_{1-6}$alkyl, $C_{3-8}$cycloalkyl, $C_{6-14}$aryl, or aralkyl;

$R^4$ is OR$^{10}$, NHR$^{10}$ or SR$^{10}$, where $R^{10}$ is hydrogen, $C_{1-6}$alkyl, $C_{3-8}$cycloalkyl, or aralkyl; or NHR$^{11}$ wherein $R^{11}$ is $C_{1-6}$alkyl, aralkyl, or $C_{6-14}$aryl;

or a pharmaceutically acceptable derivative thereof, and their use in the treatment of viral infections.

A further aspect of the present invention features a compound of formula (III)

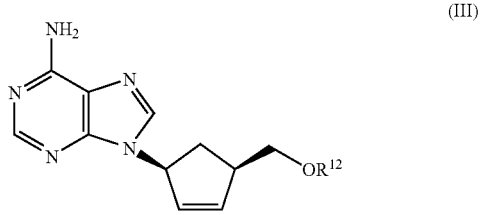

wherein R¹² is

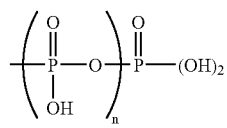

wherein n is 0, 1, or 2, and wherein $R^{12}$ is optionally substituted by $C_{6-14}$aryl.

The compounds of the present invention include diastereomers differing in the absolute configuration at phosphorus. Diastereomers may be present as a single isomer or as mixtures of diastereomers.

The term "alkyl" refers to a straight-chain or branched-chain saturated aliphatic hydrocarbon radical containing the specified number of carbon atoms, or where no number is specified, preferably from 1 to about 10, more preferably from 1 to about 8 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl," alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, propenyl, isopropenyl, butenyl, isobutyenyl, pentenyl, hexenyl, hexadienyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like, with methoxy being preferred.

The term "halo" or "halogen" refers to a radical of fluorine, chlorine, bromine or iodine.

The term "aryl" refers to a carbocyclic aromatic radical (such as phenyl or naphthyl) containing the specified number of carbon atoms, preferably from 6–14 carbon atoms, and more preferably from 6–10 carbon atoms, optionally substituted with one or more substituents selected from $C_{1-6}$ alkoxy (for example, methoxy), nitro, halogen (for example chloro), amino, carboxylate and hydroxy. Examples of aryl radicals include, but are not limited to phenyl, naphthyl, indenyl, indanyl, azulenyl, fluorenyl, anthracenyl and the like.

The term "heterocycle", alone or in combination with another term, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5–7 membered monocyclic heterocycles and 8–10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

The term "pharmaceutically acceptable derivative", as used herein, means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Compounds of formula (I), (II), and (III) and their pharmaceutically acceptable derivatives may hereinafter be referred to as compounds according to the invention.

Preferred compounds of formulae (I) and (II) include the compounds listed in Table 1.

TABLE 1

[Structure: adenine attached to cyclopentene ring with CH2-O-P(=O)(OR¹)(N(R⁵)-C(R²)(R³)-C(=O)-R⁴)]

| Example | R¹ | R² | R³ | R⁴ | R⁵ |
|---|---|---|---|---|---|
| 2 | Ph | H | Me | OMe | H |
| 3 | Ph | H | Me | OEt | H |
| 4 | Ph | Me | H | OMe | H |
| 5 | Ph | H | Me | OCH$_2$Ph | H |
| 6 | Ph | H | CH$_2$Ph | OMe | H |
| 7 | Ph | H | CH$_2$Ph | OEt | H |
| 8 | H | H | CH$_2$Ph | OH | H |
| 9 | Ph | Me | Me | OMe | H |
| 10 | Ph | H | CH$_2$Ph(4-O-t-Bu) | OMe | H |
| 11 | Ph | H | Me | O-i-Pr | H |
| 12 | Ph | H | Me | O-t-Bu | H |
| 13 | Ph | H | Me | OCH$_2$-t-Bu | H |
| 14 | Ph | H | Me | OCH$_2$-cyclopropyl | H |
| 15 | Ph | H | CH$_2$CHMe$_2$ | OMe | H |
| 16 | Ph | H | CH$_2$Ph(4-OMe) | OMe | H |
| 17 | Ph | CH$_2$Ph | H | OMe | H |
| 18 | Ph | CH$_2$CHMe$_2$ | H | OMe | H |
| 19 | Ph | CH$_2$-(1H-indol-3-yl) | H | OMe | H |
| 20 | Ph | CH$_2$-(1H-indol-3-yl) | H | OMe | H |
| 21 | Ph | CHMe$_2$ | H | OMe | H |
| 22 | Ph | CH$_2$CO$_2$Me | H | OMe | H |
| 23 | Ph | H | R³/R⁵ = (CH$_2$)$_3$ | OMe | — |
| 24 | Ph | H | CH(Me)Et | OMe | H |
| 25 | Ph | H | n-Pr | OMe | H |
| 25 | Ph | H | CH$_2$Ph | O-i-Pr | H |
| 27 | Ph | H | CH$_2$Ph | O-t-Bu | H |
| 28 | Ph | H | CH$_2$Ph | OCH$_2$-t-Bu | H |
| 29 | Ph | H | CH$_2$Ph | OCH$_2$Ph | H |
| 30 | (2-CO$_2$Me)Ph | H | Me | OMe | H |
| 31 | (4-PhCOCH=CH)Ph | H | Me | OMe | H |
| 32 | Ph | H | H | OMe | H |
| 33 | Ph | H | i-Pr | OMe | H |
| 34 | Ph | H | CH$_2$CH$_2$SMe | OMe | H |
| 35 | Ph | Me | Me | OEt | H |
| 36 | Ph | Me | Me | O-i-Pr | H |
| 37 | Ph | Me | Me | OCH$_2$-t-Bu | H |
| 38 | Ph | — | R²/R³ = (CH$_2$)$_4$ | OMe | H |
| 39 | Ph | — | R²/R³ = (CH$_2$)$_5$ | OMe | H |
| 40 | Ph | H | CH$_2$CO$_2$Me | OMe | H |

TABLE 1-continued

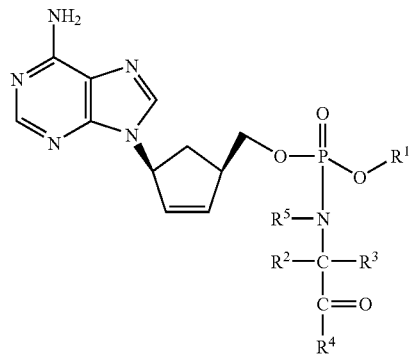

| Example | R¹ | R² | R³ | R⁴ | R⁵ |
|---------|------|------|------|------|------|
| 41 | (4-Cl)Ph | H | Me | OMe | H |
| 42 | H | Me | H | NHMe | H |

Preferred compounds of the present invention include (1R,cis)-4-(6-Amino-9H-purin-9-yl)-2-cyclopentene-1-methanol O-(phenyl methoxy-L-alaninyl)phosphoramidate;

(1R,cis)-4-(6-Amino-9H-purin-9-yl)-2-cyclopentene-1-methanol O-(phenyl ethoxy-L-alaninyl)phosphoramidate;

(1R,cis)-4-(6-Amino-9H-purin-9-yl)-2-cyclopentene-1-methanol O-(phenyl methoxy-D-alaninyl)phosphoramidate;

(1R,cis)-4-(6-Amino-9H-purin-9-yl)-2-cyclopentene-1-methanol O-(phenyl benzyloxy-L-alaninyl)phosphoramidate;

(1R,cis)-4-(6-Amino-9H-purin-9-yl)-2-cyclopentene-1-methanol O-(phenyl methoxy-L-phenylalaninyl)phosphoramidate;

(1R,cis)-4-(6-Amino-9H-purin-9-yl)-2-cyclopentene-1-methanol O-(phenyl ethoxy-L-phenylalaninyl)phosphoramidate;

(1R,cis)-4-(6-Amino-9H-purin-9-yl)-2-cyclopentene-1-methanol O-(L-phenylalaninyl)phosphoramidate Disodium Salt;

(1R,cis)-4-(6-Amino-9H-purin-9-yl)-2-cyclopentene-1-methanol O-(phenyl methoxy-α, α,-dimethylglycinyl)phosphoramidate;

(1R,cis)-4-(6-Amino-9H-purin-9-yl)-2-cyclopentene-1-methanol O-[phenyl methoxy-L-(O-tert-butyltyrosinyl)]phosphoramidate;

(1R,cis)-4-(6-Amino-9H-purin-9-yl)-2-cyclopentene-1-methanol O-(phenyl isopropoxy-L-alaninyl)phosphoramidate;

(1R,cis)-4-(6-Amino-9H-purin-9-yl)-2-cyclopentene-1-methanol O-(phenyl tert-butoxy)-L-alaninyl)phosphoramidate;

(1R,cis)-4-(6-Amino-9H-purin-9-yl)-2-cyclopentene-1-methanol O-[phenyl (2,2-dimethylpropoxy)-L-alaninyl]phosphoramidate;

(1R,cis)-4-(6-Amino-9H-purin-9-yl)-2-cyclopentene-1-methanol O-(phenyl cyclopropylmethoxy-L-alaninyl)phosphoramidate;

(1R,cis)-4-(6-Amino-9H-purin-9-yl)-2-cyclopentene-1-methanol O-(phenyl methoxy-L-leucinyl)phosphoramidate;

(1R,cis)-4-(6-Amino-9H-purin-9-yl)-2-cyclopentene-1-methanol O-[phenyl methoxy-L-(O-methyltyrosinyl)]phosphoramidate;

(1R,cis)-4-(6-Amino-9H-purin-9-yl)-2-cyclopentene-1-methanol O-(phenyl methoxy-D-phenylalaninyl)phosphoramidate;

(1R,cis)-4-(6-Amino-9H-purin-9-yl)-2-cyclopentene-1-methanol O-(phenyl methoxy-D-leucinyl)phosphoramidate;

(1R,cis)-4-(6-Amino-9H-purin-9-yl)-2-cyclopentene-1-methanol O-(phenyl methoxy-D-tryptophanyl)phosphoramidate;

(1R,cis)-4-(6-Amino-9H-purin-9-yl)-2-cyclopentene-1-methanol O-(phenyl methoxy-D-tryptophanyl)phosphoramidate;

(1R,cis)-4-(6-Amino-9H-purin-9-yl)-2-cyclopentene-1-methanol O-(phenyl methoxy-D-valinyl)phosphoramidate;

(1R,cis)-4-(6-Amino-9H-purin-9-yl)-2-cyclopentene-1-methanol O-(phenyl dimethoxy-D-aspartyl)phosphoramidate;

(1R,cis)-4-(6-Amino-9H-purin-9-yl)-2-cyclopentene-1-methanol O-(phenyl methoxy-L-prolinyl)phosphoramidate;

(1R,cis)-4-(6-Amino-9H-purin-9-yl)-2-cyclopentene-1-methanol O-(phenyl methoxy-L-isoleucinyl)phosphoramidate;

(1R,cis)-4-(6-Amino-9H-purin-9-yl)-2-cyclopentene-1-methanol O-(phenyl methoxy-L-norvalinyl)phosphoramidate;

(1R,cis)-4-(6-Amino-9H-purin-9-yl)-2-cyclopentene-1-methanol O-(phenyl isopropoxy-L-phenylalaninyl)phosphoramidate;

(1R,cis)-4-(6-Amino-9H-purin-9-yl)-2-cyclopentene-1-methanol O-(phenyl tert-butoxy-L-phenylalaninyl)phosphoramidate;

(1R,cis)-4-(6-Amino-9H-purin-9-yl)-2-cyclopentene-1-methanol O-[phenyl (2,2-dimethylpropoxy)-L-phenylalaninyl]phosphoramidate;

(1R,cis)-4-(6-Amino-9H-purin-9-yl)-2-cyclopentene-1-methanol O-(phenyl benzyloxy-L-phenylalaninyl)phosphoramidate;

(1R,cis)-4-(6-Amino-9H-purin-9-yl)-2-cyclopentene-1-methanol O-[(2-carbomethoxy)phenyl methoxy-L-alaninyl]phosphoramidate;

(1R,cis)-4-(6-Amino-9H-purin-9-yl)-2-cyclopentene-1-methanol O-[4-(3-oxo-3-phenylpropenylphenyl methoxy-L-alaninyl]phosphoramidate;

(1R,cis)-4-(6-Amino-9H-purin-9-yl)-2-cyclopentene-1-methanol O-(phenyl methoxyglycinyl)phosphoramidate;

(1R,cis)-4-(6-Amino-9H-purin-9-yl)-2-cyclopentene-1-methanol O-(phenyl methoxy-L-valinyl)phosphoramidate;

(1R,cis)-4-(6-Amino-9H-purin-9-yl)-2-cyclopentene-1-methanol O-[phenyl(methoxy)-L-methioninyl)phosphoramidate;

(1R,cis)-4-(6-Amino-9H-purin-9-yl)-2-cyclopentene-1-methanol O-(phenyl ethoxy-α,α,-dimethylglycinyl)phosphoramidate;

(1R,cis)-4-(6-Amino-9H-purin-9-yl)-2-cyclopentene-1-methanol O-(phenyl isopropoxy-α,α-dimethylglycinyl) phosphoramidate;

(1R,cis)-4-(6-Amino-9H-purin-9-yl)-2-cyclopentene-1-methanol O-[phenyl (2,2-dimethylpropoxy)-α,α-dimethylglycinyl]phosphoramidate;

(1R,cis)-4-(6-Amino-9H-purin-9-yl)-2-cyclopentene-1-methanol O-(phenyl methoxy-cyclopentaneglycinyl) phosphoramidate;

(1R,cis)-4-(6-Amino-9H-purin-9-yl)-2-cyclopentene-1-methanol O-(phenyl methoxy-cyclohexaneglycinyl)phosphoramidate;

(1R,cis)-4-(6-Amino-9H-purin-9-yl)-2-cyclopentene-1-methanol O-(phenyl dimethoxy-L-aspartyl)phosphoramidate;

(1R,cis)-4-(6-Amino-9H-purin-9-yl)-2-cyclopentene-1-methanol O-[(4-chloro)phenyl methoxy-L-alaninyl]phosphoramidate;

(1R,cis)-4-(6-Amino-9H-purin-9-yl)-2-cyclopentene-1-methanol O-[L-(N-methyl)amino)alaninyl]phosphoramidate sodium salt;

and pharmaceutically acceptable derivatives thereof.

A further aspect of the present invention features a compound of formula (II) wherein $R^1$ is H or $C_{6-14}$aryl, $R^2$ is $C_{1-6}$alkyl or aralkyl, $R^3$ is hydrogen, $C_{1-6}$alkyl or aralkyl and $R^4$ is $OR^{10}$ wherein $R^{10}$ is $C_{1-6}$alkyl or $C_{3-8}$cycloalkyl.

A preferred aspect of the present invention features a compound of formula (II) wherein $R^1$ is $C_{6-14}$aryl, $R^2$ is methyl, $R^3$ is hydrogen, and $R^4$ is $OR^{10}$ where $R^{10}$ is methyl or ethyl. More preferably, $R^1$ is phenyl.

In another aspect of the present invention there is provided compounds of formula (II) wherein $R^1$ is hydrogen.

In another aspect of the present invention there is provided compounds of formula (I) and (II) wherein $R^2$ and $R^3$ are not both hydrogen.

When $R^2$ and $R^3$ are different, the L-configuration of naturally occurring amino acids is preferred.

More preferred compounds of the present invention include (1R,cis)-4-(6-Amino-9H-purin-9-yl)-2-cyclopentene-1-methanol O-(phenyl methoxy-L-alaninyl)phosphoramidate;

(1R,cis)-4-(6-Amino-9H-purin-9-yl)-2-cyclopentene-1-methanol O-(phenyl ethoxy-L-alaninyl)phosphoramidate;

(1R,cis)-4-(6-Amino-9H-purin-9-yl)-2-cyclopentene-1-methanol O-(phenyl methoxy-D-alaninyl)phosphoramidate;

(1R,cis)-4-(6-Amino-9H-purin-9-yl)-2-cyclopentene-1-methanol O-(phenyl benzyloxy-L-alaninyl)phosphoramidate;

(1R,cis)-4-(6-Amino-9H-purin-9-yl)-2-cyclopentene-1-methanol O-(phenyl methoxy-L-phenylalaninyl)phosphoramidate;

(1R,cis)-4-(6-Amino-9H-purin-9-yl)-2-cyclopentene-1-methanol O-(phenyl ethoxy-L-phenylalaninyl)phosphoramidate;

(1R,cis)-4-(6-Amino-9H-purin-9-yl)-2-cyclopentene-1-methanol O-(L-phenylalaninyl) phosphoramidate Disodium Salt;

(1R,cis)-4-(6-Amino-9H-purin-9-yl)-2-cyclopentene-1-methanol O-(phenyl methoxy-α,α,-dimethylglycinyl) phosphoramidate;

and pharmaceutically acceptable derivatives thereof.

Pharmaceutically acceptable salts of the compounds of the present invention include salts of a basic or acidic portion of the molecule. Salts of a basic moiety may be formed by organic carboxylic acids such as acetic, lactic, tartaric, malic, isethionic, lactobionic, and succinic acids, organic sulphonic acids, such as methanesulphonic, ethanesulphonic, benzenesulphonic and p-toluenesulphonic acids and inorganic acids, such as hydrochloric, sulphuric, phosphoric and sulphamic acids. Salts of an acidic moiety may be formed by an appropriate base, such as an alkali metal (for example, sodium), an alkaline earth (for example, magnesium, calcium), ammonium and ammonium salts.

Preferred esters of the compounds according to the invention may be independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Esters of carboxylate may include alkyl, cycoalkyl, aralkyl, and aryl esters.

Compounds of formula (I) and (II) may be made by modifications of the procedures described in Biochem. Biophys. Res. Commun. 225:363–369, 1997.

The present invention further includes a process for the preparation of a compound of formula (I) which comprises reaction of a compound of formula (IV)

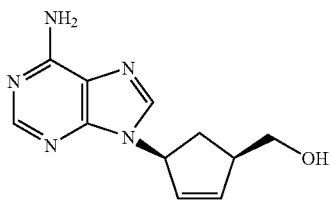

with a compound of formula (VI)

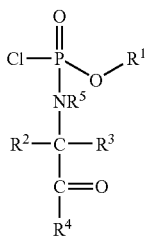

wherein R¹–R⁵ are as hereinbefore defined for formula (I).

The reaction may be carried out in pyridine, pyridine-tetrahydrofuran or acetonitrile in the presence of t-butyl magnesium chloride (Balzarini et al., *Biochem. Biophys. Res. Comm.* 225:363–369 (1996). The phosphochloridate intermediates, compounds of formula (VI), may be prepared according to WO 96/29336, incorporated herein by reference hereto; McGuigan et al, J. Med. Chem., 1996, 39, 1748–1753; and McGuigan et al, Antiviral Res., 1997, 35, 195–204.

Compounds of formula (IV) may be made according to Example 1 or by any method known in the art.

The present invention further includes a process for the preparation of a compound of formula (II) which comprises reaction of a compound of formula (IV)

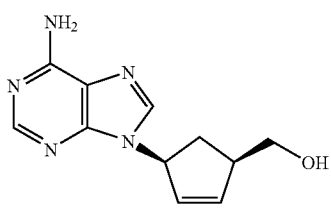

with a compound of formula (V)

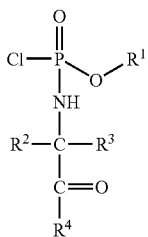

wherein R¹–R⁴ are as hereinbefore defined for formula (II).

The reaction may be carried out in pyridine, pyridine-tetrahydrofuran or acetonitrile in the presence of t-butyl magnesium chloride (Balzarini et al., *Biochem. Biophys. Res. Comm.* 225:363–369 (1996). The phosphochloridate intermediates, compounds of formula (V), may be prepared according to WO 96/29336, incorporated herein by reference hereto; McGuigan et al, J. Med. Chem., 1996, 39, 1748–1753; and McGuigan et al, Antiviral Res., 1997, 35, 195–204.

O-monophosphate compounds of formula (III) may be prepared by treating a compound of formula (IV) with an appropriate phosphorylating agent, e.g. phosphoryl chloride as in M. Yoshikawa, T. Kato and T. Takenishi, Bulletin Chem. Soc. Japan, 1969, 42, 3505. The corresponding O-di and O-triphosphates may be prepared by the method of N. C. Mishra and A. D. Broom, J. Chem. Soc., Chem. Commun., 1991, 1276 or by the methods described in "Nucleotide Analogs" K. H. Sheit, John Wiley and Sons, New York 1980, pp. 211–215, and D. E. Hoard and D. G. Ott, J. Amer, Chem. Soc. 1965, 87, 1785.

Compounds of formula (III) may also be prepared by any method known in the art.

Separation of isomers may be accomplished by methods known in the art, for example, by high-pressure liquid chromatography with chiral columns, particularly using liquid carbon dioxide as the mobile phase, or by crystallization of salts with chiral acids or bases.

Phosphate isomers may be separated with Supercritical Fluid Chromatography using a Chiralpak AS column, 25% methanol in carbon dioxide as the eluent, flow rate 2 mL/min, temperature 40° C., and pressure 3000 psi.

One aspect of the invention features the compounds according to the invention for use in medical therapy, particularly for the treatment or prophylaxis of retroviral infections and hepatitis B virus infections.

A further aspect of the invention features the compounds according to the invention for use in the manufacture of a medicament for the treatment or prophylaxis of viral infections, particularly for the treatment of retroviral infections, for example HIV infections, and hepatitis B virus infections.

In a further aspect of the present invention there is provided a method for the treatment of viral infections, for example, retroviral infections, particularly HIV infections, and hepatitis B virus infections in a host comprising administering to said host a therapeutically effective amount of a compound according to the invention.

Examples of retroviral infections which may be treated or prevented in accordance with the invention include human retroviral infections such as human immunodeficiency virus (HIV), HIV-1, HIV-2 and human T-cell lymphotropic virus (HTLV), for example, HTLV-I or HTLV-II infections. The compounds according to the invention are especially useful for the treatment of AIDS and related clinical conditions such as AIDS-related complex (ARC), progressive generalized lymphadenopathy (PGL), Kaposi's sarcoma, AIDS-related neurological conditions, such as multiple sclerosis, tropical paraparesis, and AIDS dementia, anti-HIV antibody-positive and HIV-positive conditions and thrombocytopenic purpura.

The compounds according to the invention are particularly applicable for the treatment of asymptomatic infections or diseases in humans caused by or associated with human retroviruses.

The compounds according to the invention may be employed in combination with other therapeutic agents for the treatment of the above infections or conditions. Other therapeutic agents may include agents that are effective for the treatment of viral infections or associated conditions such as reverse transcriptase inhibitors, for example, zidovudine or abacavir; (1 alpha, 2 beta, 3 alpha)-9-[2,3-bis(hydroxymethyl)cyclobutyl]guanine [(−)BHCG, SQ-34514]; oxetanocin-G (3,4-bis-(hydroxymethyl)-2-oxetanosyl]guanine); acyclic nucleosides (e.g. acyclovir, valaciclovir, famciclovir, ganciclovir, penciclovir); acyclic nucleoside phosphonates (e.g. (S)-1-(3-hydroxy-2-phosphonyl-methoxypropyl)cytosine (HPMPC) or PMEA or PMPA; ribonucleotide reductase inhibitors such as hydroxyurea, 2-acetylpyridine 5-[(2-chloroanilino)thiocarbonyl) thiocarbonohydrazone; other 2',3'-dideoxynucleosides such as 2',3'-dideoxycytidine, 2',3'-dideoxyadenosine, 2',3'-dideoxyinosine, 3'-deoxy-2',3'-didehydrothymidine (d4T); protease inhibitors such as saquinavir, indinavir, ritonavir, nelfinavir, amprenavir; oxathiolane nucleoside analogues such as lamivudine, cis-1-(2-(hydroxymethyl)-1,3-oxathiolan-5-yl)-5-fluorocytosine (FTC); 3'-deoxy-3'-fluorothymidine, 5-chloro-2',3'-dideoxy-3'-fluorouridine, ribavirin, 9-[4-hydroxy-2-(hydroxymethyl)but-1-yl]-guanine (H2G); tat inhibitors such as 7-chloro-5-(2-pyrryl)-3H-1,4-benzodiazepin-2-(H)one (Ro5-3335), 7-chloro-1,3-dihydro-5-(1H-pyrrol-2yl)-3H-1,4-benzodiazepin-2-amine (Ro24-7429); interferons such as α-interferon; renal excretion inhibitors such as probenecid; nucleoside transport inhibitors such as dipyridamole; pentoxifylline, N-acetylcysteine (NAC), Procysteine, α-trichosanthin, phosphonoformic acid, as well as immunomodulators such as interieukin II or thymosin, granulocyte macrophage colony stimulating factors, erythropoetin, soluble $CD_4$ and genetically engineered derivatives thereof; or non-nucleoside reverse transcriptase inhibitors (NNRTIs) such as nevirapine (BI-RG-587), loviride (α-APA) and delavuridine (BHAP), and phosphonoformic acid, and 1,4-dihydro-2H-3,1-benzoxazin-2-ones NNRTIs such as (−)-6-chloro-4-cyclopropylethynyl-4-trifluoromethyl-1,4-dihydro-2H-3,1-benzoxazin-2-one (L-743,726 or DMP-266), and quinoxaline NNRTIs such as isopropyl (2S)-7-fluoro-3,4-dihydro-2-ethyl-3-oxo-1(2H)-quinoxalinecarboxylate (HBY1293). The component compounds of such combination therapy may be administered simultaneously, in either separate or combined formulations, or at different times, for example, sequentially such that a combined effect is achieved.

Another aspect of the present invention features a method of delivering a compound of formula (III), wherein $R^{12}$ and n are defined as above, into cells by treating said cells with a compound of formula (I) or (II) as defined above. The cells to be treated may be within a human or ex vivo, for example, in culture.

The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

The amounts required of the active ingredient will depend upon a number of factors including the severity of the condition to be treated and the identity of the recipient and will ultimately be at the discretion of the attendant physician or veterinarian. In general however, for each of these utilities and indications, a suitable effective dose of a compound of formula (I) will be in the range of 0.01 to 200 mg per kilogram body weight of recipient per day, advantageously in the range of 1 to 100 mg per kilogram body weight per day.

The desired dose is preferably presented as one, two, three or four or more subdoses administered at appropriate intervals throughout the day. These sub-doses may be administered in unit dosage forms, for example, containing about 0.5 to 2000 mg, preferably about 5, 25, 50, 150, 200, or 250 mg of active ingredient per unit dose form.

A further aspect of the present invention features a patient pack comprising at least one active ingredient selected from a compound of formula (I), (II), and (III) and an information insert containing directions on the use of the compound.

While it is possible for the active ingredient to be administered alone, it is preferable to present it as a pharmaceutical composition. A further aspect of the present invention features pharmaceutical compositions comprising a compound of formula (I), (II) or (III) or a pharmaceutically acceptable derivative thereof and a pharmaceutically acceptable carrier therefor.

The compositions of the present invention comprise at least one active ingredient, as defined above, together with one or more pharmaceutically acceptable carriers thereof and optionally other therapeutic agents. Each carrier must be "acceptable" in the sense of being compatible with the other ingredients of the composition and not deleterious to the recipient thereof. Compositions include those suitable for oral, rectal, nasal, topical (including buccal and sublingual), vaginal or parenteral (including subcutaneous, intramuscular, intravenous and intradermal) administration.

The compositions may conveniently be presented in unit dosage form prepared by any of the methods well known in the art of pharmacy. Such methods include the step of bringing into association the active ingredient with the carrier which constitutes one or more accessory ingredients. In general, the compositions are prepared by uniformly and intimately bringing in to association the active ingredient with liquid carriers or finely divided solid carriers or both, and then, if necessary, shaping the product.

Compositions of the present invention suitable for oral administration may be presented as discrete units such as capsules, cachets, sachets of granules or tablets (such as a swallowable, dispersible or chewable tablet) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored any may be formulated so as to provide slow or controlled release of the active ingredient therein. Tablets may be enteric coated.

Compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions for rectal administration may be presented as a suppository with a suitable base comprising for example cocoa butter or a salicylate.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solution which may contain anti-oxidants, buffers, bacteriostats and solutes which render the formulation aqueous and non-aqueous sterile suspensions which may include suspending agents and thickening agents. The compositions may be presented in unit-dose or multidose sealed containers, for example, ampoules and vial, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The active ingredient may also be presented in a composition comprising micrometer- or nanometer-size particles of active ingredient.

Preferred unit dosage compositions are those containing a daily dose or unit daily sub-dose (as herein above recited) or an appropriate fraction thereof, of the active ingredient.

It should be understood that in addition to the ingredients particularly mentioned above the composition of this invention may include other agents conventional in the art having regard to the type of formulation in question, for example those suitable for oral administration may include flavoring agents or taste masking agents.

A further aspect of the invention relates to kits to be used in the treatment of patients suffering from viral infections. These kits include one or more oral dosages of a compound of formula (I), (II), or (III) and may include one or more additional therapeutic agents. By way of illustration, a kit of the invention may include one or more tablets, capsules, caplets, gelcaps or liquid formulations containing a compound of formula (I) and one or more tablets, capsules, caplets, gelcaps or liquid formulations containing a compound of formula (I) in dosage amounts within the ranges described above. The kits may include as an insert printed dosing information for the co-administration of the agents.

The following examples are intended for illustration only and are not intended to limit the scope of the invention in any way.

EXAMPLE 1

(1R,cis)-4-(6-Amino-9H-purin-9-yl)-2-cyclopentene-1-methanol (a) (1S,4R)-tert-Butyl 3-oxo-2-azabicyclo[2.2.1]hept-5-ene-2-carboxylate (+)-2-Azabicyclo[2.2.1]hept-5-en-3-one (Chiroscience, Cambridge, England; 54.565 g, 0.500 mole) was dissolved in dry tetrahydrofuran (350 ml). Di-tert-butyl carbonate (Aldrich, 114.87 g, 0.510 mole as 97%) and 4-dimethylaminopyridine (Aldrich, 600 mg) were added to the stirred mixture. The resulting solution was stirred at ambient temperature for 2 hours. Solvent was evaporated under reduced pressure and the residual orange solid was crystallized from toluene-hexanes to give title compound as white crystals (95.72 g, 91%), m.p. 85–86° C.; $^1$H-NMR (CDCl$_3$) δ 1.50 (s, 9H), 2.24 (app AB q, J=8.4 Hz, 2H), 3.39 (br s, 1H), 4.96 (m, 1H), 6.66 (m, 1H), 6.89 (m, 1H).

Anal. Calcd. for $C_{11}H_{15}NO_3$: C, 63.14; H, 7.21; N, 6.69. Found: C, 63.20; H, 7.26; N, 6.65.

(b) (1S,cis)-tert-Butyl N-[4-(hydroxymethyl)-2-cyclopenten-1-yl]carbamate

A solution of (1S,4R)-tert-butyl 3-oxo-2-azabicyclo[2.2.1]hept-5-ene-2-carboxylate (part a of this example, 95.50 g, 0.456 mole) in tetrahydrofuran (500 ml)-water (50 ml) was added over 10 minutes to a vigorously stirred solution of sodium borohydride (Aldrich, 21.96 g, 0.580 mole as 99%) in water (100 ml). The temperature was maintained below 35° C. After 2 hours, the solution was cooled to maintain the temperature below 25° C. while concentrated hydrochloric acid (50 ml) was added over 10 minutes. Additional water (100 ml) was added to dissolve solid and the solution was extracted with toluene (4×300 ml). The combined organic layers were washed with 9:1 saturated sodium sulfate/saturated sodium carbonate (200 ml) and dried (sodium sulfate). Evaporation of solvents under reduced pressure left a colorless syrup which crystallized on stirring with hexanes (200 ml) to provide title compound as a fine white powder (87.16 g, 90%), m.p. 72–73° C.; $^1$H-NMR (DMSO-d$_6$) δ 6.78 (d, J=7.6 Hz, 1H), 5.80 and 5.60 (two m, 2H), 4.58 (t, J=5.25 Hz, 2H), 4.45 (m, 1H), 3.35 (m overlapping water), 2.60 (m, 1H), 2.30 (m, 1H), 1.38 (s, 9H), 1.20 (m, 1H); $[\alpha]_{589}^{20}$+2.80° (c 5.0, methanol).

Anal. Calcd. for $C_{11}H_{19}NO_3$: C, 61.95; H, 8.98; N, 6.57. Found: C, 61.87; H, 8.97; N, 6.55.

(c) (1R,cis)-4-Amino-2-cyclopentene-1-methanol hydrochloride (1S,cis)-tert-Butyl N-[4-(hydroxymethyl)-2-cyclopenten-1-yl]carbamate (part b of this example, 10.66 g, 50.0 mmol) was refluxed in absolute ethanol (25 mL) with concentrated hydrochloric acid (5.0 mL, 60 mequiv) for 2.5 hours. Evaporation of volatiles left title compound as white solid; mass spectrum (ES): 114 (M+1); $^1$H-NMR (DMSO-d$_6$) δ 7.9 (m, 3H), 6.03 and 5.75 (two m, 2H), 4.11 (m, 1H), 3.41 (d, J=5.4 Hz, 2H), 2.8 (m, 1H), 2.36 (m, 1H), 1.4 (m, 1H). This solid was used immediately in the following example.

(d) (1R,cis)-4-[(5-Amino-6-chloro-4-pyrimidinyl)amino]-2-cyclopentene-1-methanol A solution of (+)-(1R,cis)-4-amino-2-cyclopentene-1-methanol hydrochloride (from deblocking of 10.66 g, 50.0 mmoles of (+)-(1S,cis)-tert-butyl N-[4-(hydroxymethyl)-2-cyclopenten-1-yl]carbamate as described in part c of this example), 5-amino-4,6-dichloropyrimidine (Aldrich, 16.40 g, 0.100 mole), and triethylamine (15.2 g, 0.150 mole) in 1-butanol (25 mL) was refluxed under nitrogen for 18 hours. The solution was cooled and 1 N sodium hydroxide (100 mL) was added. Volatiles were evaporated under reduced pressure and the residual solid was chromatographed on silica gel. Title compound eluted with 5% methanol-chloroform as a pale yellow glass (10.8 g). Crystallization of such a sample from ethyl acetate gave title compound as white needles, m.p. 144–146° C.; $^1$H-NMR (DMSO-d$_6$) δ

7.75 (s, 1H), 6.76 (d, J=6.8 Hz, 1H), 5.93 and 5.82 (two m, 2H), 5.11 (m, 3H), 4.66 (t, J=5.3 Hz, 1H), 3.40 (br t, J=6.1 Hz, 2H), 2.75 (m, 1H), 2.20 (m, 1H), 1.38 (m, 1H).

Anal. Calcd. for $C_{10}H_{13}N_4ClO$: C, 49.90; H, 5.44; N, 23.28. Found: C, 49.92; H, 5.57; N, 23.10.

(e) (1R,cis)-4-(6-Chloro-9H-purin-9-yl)-2-cyclopentene-1-methanol (1R,cis)-4-[(5-Amino-6-chloro-4-pyrimidinyl)amino]-2-cyclopentene-1-methanol (from part d of this example, 9.63 g, 40.0 mmol), triethylorthoformate (150 mL), and concentrated hydrochloric acid (14 mL) were stirred for 3 hours. Volatiles were evaporated and the residual solid was partitioned between chloroform (300 mL) and saturated aqueous sodium carbonate (100 mL). The aqueous layer was extracted with chloroform (2×100 mL). The combined chloroform layers were dried (sodium sulfate). Volatiles were evaporated under reduced pressure and the residual yellow glass was chromatographed on silica gel. Elution with ethyl acetate gave title compound as white needles from ethyl acetate (7.45 g, 74%), m.p. 121–124° C.; $^1$H-NMR (DMSO-d$_6$) δ 8.81 (s, 1H), 8.64 (s, 1H), 6.24 and 6.21 (two m, 2H), 5.75 (m, 1H), 4.75 (t, J=5.4 Hz, 1H), 3.34 (m, 2H), 2.95 (m, 1H), 2.75 (m, 1H), 1.75 (m, 1H).

Anal. Calcd. for $C_{11}H_{11}N_4ClO$: C, 52.70; H, 4.42; N, 22.35; Cl, 14.14. Found: C, 52.81; H, 4.46; N, 22.31; 14.22.

(f) (1R,cis)-4-(6-Amino-9H-purin-9-yl)-2-cyclopentene-1-methanol (1R,cis)-4-(6-Chloro-9H-purin-9-yl)-2-cyclopentene-1-methanol (from part e of this example, 2.00 g, 7.98 mmol) was stirred in liquid ammonia (50 mL) in a Parr bomb at 25° C. for 18 hours. Evaporation of volatiles and crystallization of the residual solid from methanol-acetonitrile gave title compound as white prisms (1.61 g, 87%), m.p. 195–200° C.; $^1$H-NMR (DMSO-d$_6$) δ 8.15 (s, 1H), 8.06 (s, 1H), 7.21 (br s, 2H), 6.15 and 5.95 (two m, 2H), 5.61 (m, 1H), 4.76 (t, J=5.4 Hz, 1H), 3.48 (t, J=5.5 Hz, 2H), 2.92 (m, 1H), 2.71 (m, 1H), 1.67 (m, 1H); $[α]_{589}^{20}$ +4.5° (c 0.5, methanol).

Anal. Calcd. for $C_{11}H_{13}N_5O$: C, 57.13; H, 5.67; N, 30.28. Found: C, 57.25; H, 5.67; N, 30.33.

EXAMPLE 2

(1R,cis)-4-(6-Amino-9H-purin-9-yl)-2-cyclopentene-1-methanol O-(phenyl methoxy-L-alaninyl) phosphoramidate (1R,cis)-4-(6-Amino-9H-purin-9-yl)-2-cyclopentene-1-methanol (part f of example 1,925 mg, 4.00 mmol) was stirred in dry pyridine (100 ml) and tert-butyl magnesium chloride (Aldrich, 1 M in tetrahydrofuran, 4.3 ml) was added. After 15 minutes, a solution of phenyl(methoxy-L-alaninyl)phosphorochloridate (prepared as described by McGuigan, C. et al., *J. Med. Chem.* 1993, 36: 1048–1052) (2.22 g, 8.00 mmol) in tetrahydrofuran (10 ml) was added. After 24 hours, additional tert-butyl magnesium chloride (4.4 ml) and phenyl(methoxy-L-alaninyl)phosphorochloridate (2.22 g) were added and stirring continued for an additional 24 hours. Volatiles were removed and the residual gummy solid was partitioned between chloroform (200 ml) and water (50 ml). The chloroform layer was dried (sodium sulfate) and concentrated to a colorless glass. The glass was chromatographed on silica gel. Title compound was eluted with 5% methanol-chloroform.

Evaporation of a methanol solution left the title compound as a white solid foam (1.02 g, 54%); high resolution mass spectrum calcd for $C_{21}H_{26}N_6O_5P$ (M+H)$^+$ m/z 473.1702, found 473.1707; $^1$H-NMR (CDCl$_3$) δ 8.39 (s, 1H), 8.04 and 7.99 (both s, 1H), 7.2 (m, 5H), 6.50 (m, 1H), 6.2 (m, 1H), 6.0 (m, 1H), 5.79 (m, 1H), 4.3–3.95 (m, 3H), 3.74 and 3.71 (two s, 3H), 3.25 (m, 1H), 2.95 (m, 1H), 1.80 (m, 1H), 1.38 and 1.37 (two d, each J=7.0 Hz, 3H); $^{31}$P-NMR (CDCl$_3$): 3.12, 2.80.

Anal. Calcd. for $C_{21}H_{25}N_6O_5P.0.19$ CH3OH.0.35H$_2$O: C, 52.49; H, 5.50; N, 17.73. Found: C, 52.51; H, 5.49; N, 17.35.

EXAMPLE 3

(1R,cis)-4-(6-Amino-9H-purin-9-yl)-2-cyclopentene-1-methanol O-(phenyl ethoxy-L-alaninyl)phosphate In the same manner as Example 2, (1R,cis)-4-(6-amino-9H-purin-9-yl)-2-cyclopentene-1-methanol (part f of example 1) was reacted with phenyl(ethoxy-L-alaninyl) phosphorochloridate (prepared as described by McGuigan, C. et al., *J. Med. Chem.* 1993, 36: 1048–1052). Title compound was eluted with 5% methanol-chloroform. Evaporation of a methanol solution left the title compound as a white solid foam; high resolution mass spectrum calcd for $C_{22}H_{28}N_6O_5P$ (M+H)$^+$ m/z 487.1859, found 187.1841; $^1$H-NMR(DMSO-d$_6$) δ 8.16 (s, 1H), 8.05 and 8.01 (both s, total 1H), 7.36 (m, 2H), 7.24 (br s, 2H), 7.19 (m, 3H), 6.13 (m, 1H), 6.02 (m, 2H), 5.63 (m, 1H), 4.03 (m overlapping q, J=7.0 Hz, 4H), 3.77 (m, 1H), 3.15 (m, 1H), 2.75 (m, 1H), 1.70 (m, 1H), 1.21 (d, J=7.1 Hz, 3H), 1.14 and 1.12 (two t, J=7.0, 7.0 Hz, total 3H); $^{31}$P-NMR (DMSO-d$_6$) 4.23, 3.88.

EXAMPLE 4

(1R,cis)-4-(6-Amino-9H-purin-9-yl)-2-cyclopentene-1-methanol O-[phenyl(methoxy)-D-alaninyl) phosphoramidate In the same manner as Example 2, (1R,cis)-4-(6-amino-9H-purin-9-yl)-2-cyclopentene-1-methanol (part f of example 1, 200 mg, 0.860 mmol) was reacted with phenyl (methoxy-D-alaninyl)phosphorochloridate (prepared as described by McGuigan, C. et al., *J. Med. Chem.* 1993, 36: 1048–1052). Title compound was eluted with 5% methanol-chloroform.

Evaporation of a methanol solution left the title compound as a white solid foam (290 mg, 71%); $^1$H-NMR (DMSO-d$_6$) δ 8.13 (s, 1H), 8.02 and 8.01 (both s, total 1H), 7.36 (m, 1H), 7.34 (m, 1H), 7.19 (m, 5H), 6.13 (m, 1H), 6.02 (m, 2H), 5.63 (m, 1H), 4.1 (m, 2H), 3.8 (m, 1H), 3.57 (s, 3H), 3.12 (m, 1H), 2.72 (m, 1H), 1.68 (m, 1H), 1.20 (m, 3H); $^{31}$P-NMR (DMSO-d$_6$) 3.96, 3.625.

Anal. Calcd. for $C_{21}H_{25}N_6O_5P.0.48H_2O$: C, 52.43; H, 5.44; N, 17.47. Found: C, 52.43; H, 5.43; N, 17.43.

EXAMPLE 5

(1R,cis)-4-(6-Amino-9H-purin-9-yl)-2-cyclopentene-1-methanol O-[phenyl(benzyloxy)-L-alaninyl) phosphoramidate In the same manner as Example 2, (1R,cis)-4-(6-amino-9H-purin-9-yl)-2-cyclopentene-1-methanol (part f of example 1, 200 mg, 0.860 mmol) was reacted with phenyl (benzyloxy-L- alaninyl)phosphorochloridate (prepared as described by McGuigan, C. et al., *J. Med. Chem.* 1993, 36: 1048–1052). Title compound was eluted with 5% methanol-chloroform. Evaporation of a methanol solution left the title compound as a white solid foam (270 mg, 57%); $^1$H-NMR (DMSO-d$_6$) δ 8.13 (s, 1H), 8.01 and 7.985 (both s, total 1H), 7.2–7.4 (m, 12H), 6.02 (m, 3H), 5.59 (m, 1H), 5.06 (m, 2H), 4.03 (m, 2H), 3.83 (m, 1H), 3.05 (m, 1H), 2.65 (m, 1H), 1.62 (m, 1H), 1.22 (d, J=7.0 Hz, 3H); $^{31}$P-NMR (DMSO-d$_6$) 4.00, 3.55.

Anal. Calcd. for $C_{27}H_{29}N_6O_5P·0.47H_2O$: C, 58.22; H, 5.42; N, 15.09. Found: C, 58.22; H, 5.44; N, 14.84.

EXAMPLE 6

(1R,cis)-4-(6-Amino-9H-purin-9-yl)-2-cyclopentene-1-methanol O-[phenyl(methoxy)-L-phenylalaninyl)phosphoramidate In the same manner as Example 2, (1R,cis)-4-(6-amino-9H-purin-9-yl)-2-cyclopentene-1-methanol (part f of example 1, 500 mg, 2.16 mmol) was reacted with phenyl (methoxy-L-phenylalaninyl)phosphorochloridate (prepared as described by McGuigan, C. et al., *J. Med. Chem.* 1993, 36: 1048–1052). Title compound was eluted with 5% methanol-chloroform.

Evaporation of a methanol solution left the title compound as a white solid foam (500 mg, 42%); $^1$H-NMR (DMSO-d$_6$) δ 8.14 and 8.13 (both s, total 1H), 8.01 and 7.985 (both s, total 1H), 7.2–7.4 (m, 5H), 6.95–7.05 (m, 5H), 7.00 and 6.98 (both br s, total 2H), 6.1 (m, 1H), 5.975 (m, 2H), 5.58 (m, 1H), 3.55–4.0 (m, 3H), 3.57 (s, 3H), 2.95 (m, 2H), 2.7 (m, 2H), 1.55 (m, 1H); $^{31}$P-NMR (DMSO-d$_6$) 3.605, 3.25.

Anal. Calcd. for $C_{27}H_{29}N_6O_5P·0.38H_2O·0.16\ CH_3CN$: C, 58.39; H, 5.42; N, 15.35. Found: C, 58.39; H, 5.41; N, 15.36.

EXAMPLE 7

(1R,cis)-4-(6-Amino-9H-purin-9-yl)-2-cyclopentene-1-methanol O-[phenyl(ethoxy)-L-phenylalaninyl)phosphoramidate In the same manner as Example 2, (1R,cis)-4-(6-amino-9H-purin-9-yl)-2-cyclopentene-1-methanol (part f of example 1, 150 mg, 0.27 mmol) was reacted with phenyl (methoxy-L-phenylalaninyl)phosphorochloridate (prepared as described by McGuigan, C. et al., *J. Med. Chem.* 1993, 36: 1048–1052). Title compound was eluted with 5% methanol-chloroform. Evaporation of a methanol solution left the title compound as a white solid foam (120 mg, 80%); $^1$H-NMR (CDCl$_3$) δ 8.38 (two s, 1H), 7.83 (two s, 1H), 7.0–7.3 (m, 10H), 6.25 (broad s, 2H), 6.10 (m, 1H), 5.92 (m, 1H), 5.70 (m, 1H), 3.7–4.3 (m, 5H), 2,6–3.2 (m, 5H), 1.60 (m, 1H), 1.17 (two t, 3H); $^{31}$P-NMR (CDCl$_3$) δ 3.86. Mass spectrum calcd for $C_{28}H_{31}N_6O_5P$ (M+H)$^+$ m/z 563, found 563.

Anal. Calcd. for $C_{28}H_{31}N_6O_5P·2/3H_2O$ C, 58.53; H, 5.67; N, 14.63. Found: C, 58.77; H, 5.51; N, 14.65.

EXAMPLE 8

(1R,cis)-4-(6-Amino-9H-purin-9-yl)-2-cyclopentene-1-methanol O-(L-phenylalaninyl)phosphoramidate Disodium Salt (1R,cis)-4-(6-Amino-9H-purin-9-yl)-2-cyclopentene-1-methanol O-[phenyl(methoxy)-L-phenylalaninyl)phosphoramidate (0.060 g, 0.11 mmoles) was suspended in solution of triethylamine (2 mL) and deionized water (2 mL) and stirred at room temperature for 18 hours. The volatiles were removed by spin evaporation in vacuo and the residue was dissolved in water (20 mL), extracted with dichloromethane (2×20 mL), and purified by anion exchange chromatography on a Sep-Pak® Vac 35cc Accell™ Plus QMA cartridge (Waters Corp., P/N WAT054725) (HCO$_3^-$ form) with an aqueous ammonium bicarbonate buffer (0–0.5 M gradient, 1 L). The appropriate fractions were combined and the volatiles were removed by spin evaporation in vacuo. The residue was twice dissolved in deionized water and spin evaporated in vacuo to give the title compound as an ammonium salt. This salt was dissolved in deionized water and passed through a Sep-Pak® Vac 20cc Accell™ Plus CM cartridge (Waters Corp., P/N WAT054675) (Na$^+$ form) using deionized water. Lyophilization of the appropriate fractions left the title compound disodium salt 3.2 hydrate as a white solid (35 mg, 510%); $^1$H-NMR (D20) δ 8.02 (s, 1H), 7.96 (s, 1H), 6.98–7.10 (m, 3H), 6.84–6.92 (m, 2H), 6.14–6.20 (m, 1H), 5.88–5.90 (m, 1H), 5.42–5.50 (m, 1H), 4.4–5.0 (br m, 3H+ HOD), 3.58–3.66 (m, 1H), 3.36–3.48 (m, 2H), 2.94–3.06 (bm, 1H), 2.64–2.78 (m, 1H), 2.40 (d, J=6.6 Hz, 2H), 1.54–1.64 (m, 1H); $^{31}$P-NMR (D20) 7.8. MS (ES$^-$) m/e 457 (MH$^-$).

Anal. Calcd. for $C_{20}H_{21}N_6Na_2O_5P·3.2H_2O$: C, 42.89; H, 4.93; N, 15.01. Found: C, 42.92; H, 4.58; N, 14.70.

EXAMPLE 9

(1R,cis)-4-(6-Amino-9H-purin-9-yl)-2-cyclopentene-1-methanol O-[phenyl(methoxy)-α,α-dimethylglycinyl)phosphoramidate In the same manner as Example 2, (1R,cis)-4-(6-amino-9H-purin-9-yl)-2-cyclopentene-1-methanol (part f of example 1, 200 mg, 0.86 mmol) was reacted with phenyl (methoxy-α,α-alaninyl)phosphorochloridate (prepared as described by McGuigan, C. et al., *J. Med. Chem.* 1993, 36: 1048–1052). Title compound was eluted with 5% methanol-chloroform. Evaporation of a methanol solution left the title compound as a white solid foam (200 mg, 48%); $^1$H-NMR (DMSO-d$_6$) δ 8.15 (s, 1H), 8.03 and 8.01 (both s, total 1H), 7.1–7.4 (m, 7H), 6.10 (m, 1H), 6.00 (m, 1H), 5.89 (m, 1H), 5.625 (m, 1H), 4.08 (m, 2H), 3.55 (s, 3H), 3.12 (m, 1H), 2.74 (m, 1H), 1.70 (m, 1H), 1.35 (m, 6H); $^{331}$P-NMR (DMSO-d$_6$) 2.43, 2.39.

Anal. Calcd. for $C_{22}H_{27}N_6O_5P·0.53H_2O·0.03\ CH_3CN$: C, 53.29; H, 5.71; N, 16.99. Found: C, 53.29; H, 5.67; N, 16.99.

The following general procedures were used in the preparation of compounds of Examples 10–41.

Standard Procedure for Phosphorochloridate Preparation

Dry triethylamine (2.0 mol equiv.) in dry dichloromethane (40 ml) was added dropwise to a stirred solution of phenyl dichlorophosphate (1.0 mol equiv.) and the appropriate amino acid ester salt (1.0 mol equiv.) in dry dichloromethane (40 ml), at −78° C. under nitrogen. Following the addition, the reaction mixture was allowed to warm slowly to room temperature and stirred overnight. The solvent was removed under reduced pressure and the crude residue was resuspended in dry diethyl ether or THF, and filtered under nitrogen. The solvent was removed under reduced pressure to leave the crude product as an oil.

All crude phosphorochloridates were used as solutions in dry THF or dry acetonitrile in subsequent coupling reactions.

Standard Procedure 1 for Phosphoramidate Preparation

To (1R,cis)-4-(6-Amino-9H-purin-9-yl)-2-cyclopentene-1-methanol (200 mg, 0.87 mmol) suspended in anhydrous acetonitrile (15 ml) under a nitrogen atmosphere, was added 1M t-butyl magnesium chloride dissolved in tetrahydrofuran (1.73 ml, 1.74 mmol). After 15 minutes, phosphorochloridate (2.61 mmol) dissolved in acetonitrile (15 ml) was added dropwise over 1 minute and the reaction mixture allowed to stir for a further 4 hours. Following the removal of volatiles in vacuo, the product was purified by column chromatography (silica) eluting with 4–5% MeOH in chloroform or dichloromethane.

Standard Procedure 2 for Phosphoramidate Preparation

To (1R,cis)-4-(6-Amino-9H-purin-9-yl)-2-cyclopentene-1-methanol (200 mg, 0.87 mmol) suspended in anhydrous tetrahydrofuran (15 ml) under a nitrogen atmosphere, was added 1M t-butyl magnesium chloride dissolved in tetrahydrofuran (1.73 ml, 1.74 mmol). After 15 minutes, phosphorochloridate (2.61 mmol) dissolved in acetonitrile (15 ml) was added dropwise over 1 minute and the reaction mixture allowed to stir for a further 4 hours. Following the removal of volatiles in vacuo, the product was purified by column chromatography (silica) eluting with 4–5% MeOH in chloroform or dichloromethane.

Standard Procedure 3 for Phosphoramidate Preparation

To (1R,cis)-4-(6-Amino-9H-purin-9-yl)-2-cyclopentene-1-methanol (200 mg, 0.87 mmol) suspended in anhydrous pyridine (15 ml) under a nitrogen atmosphere, was added 1M t-butyl magnesium chloride dissolved in tetrahydrofuran (1.73 ml, 1.74 mmol). After 15 minutes, phosphorochloridate (2.61 mmol) dissolved in acetonitrile (15 ml) was added dropwise over 1 minute and the reaction mixture allowed to stir for a further 4 hours. Following the removal of volatiles in vacuo, the product was purified by column chromatography (silica) eluting with 4–5% MeOH in chloroform or dichloromethane.

EXAMPLE 10

(1R,cis)-4-(6-Amino-9H-purin-9-yl)-2-cyclopentene-1-methanol O-[phenyl methoxy-L-(O-tert-butyltyrosinyl)]phosphoramidate Synthesis according to standard procedure 1. Title compound isolated as a brittle white foam (60%); $\delta_P$ 3.98, 4.04; $\delta_H$ 1.32 (9H, s), 1.64 (1H, m), 2.83 (1H, m), 2.95 (2H, m), 3.08 (1H, m), 3.61, 3.66 (3H, s), 4.07 (4H, m), 5.73 (1H, m), 5.94 (1H, m), 6.11 (1H, m), 6.39 (2H, br s), 6.88 (2H, d), 6.98 (2H, d), 7.16 (2H, m), 7.29 (3H, m), 7.84,7.88 (1H, s), 8.37,8.38 (1H, s); m/z (ES+) 643.2405 (MH$^+$, $C_{31}H_{37}N_6O_6NaP$ requires 643.2410).

EXAMPLE 11

(1R,cis)-4-(6-Amino-9H-purin-9-yl)-2-cyclopentene-1-methanol O-(phenyl isopropoxy-L-alaninyl)phosphoramidate Synthesis according to standard procedure 1. Title compound isolated as a brittle white foam (89%); $\delta_P$ 3.97, 4.20; $\delta_H$ 1.14 (6H, m), 1.31 (3H, m), 1.63 (1H, m), 2.79 (1H, m), 3.12 (1H, m), 4.05 (3H, m), 4.92 (1H, m), 5.66 (1H, m), 5.87 (1H, m), 6.08 (1H, m), 6.22 (2H, br s), 7.06 (2H, m), 7.19 (3H, m), 7.78, 7.82 (1H, s), 8.29 (1H, s); m/z (ES+) 523.1832 (MH$^+$, $C_{23}H_{29}N_6O_5NaP$ requires 523.1835).

EXAMPLE 12

(1R,cis)-4-(6-Amino-9H-purin-9-yl)-2-cyclopentene-1-methanol O-(phenyl tert-butoxy-L-alaninyl)phosphoramidate Synthesis according to standard procedure 1. Title compound isolated as a brittle white foam (59%); $\delta_P$ 4.10, 4.27; $\delta_H$ 1.24 (3H, m), 1.35 (9H, s), 1.54 (1H, m), 2.79 (1H, m), 3.13 (1H, m), 3.80 (1H, m), 4.09 (3H, m), 5.66 (1H, m), 5.87 (1H, m), 6.08 (1H, m), 6.22 (2H, br s), 7.15 (5H, m), 7.78, 7.82 (1H, s), 8.29 (1H, s); m/z (ES+) 537.2001 (MH$^+$, $C_{24}H_{31}N_6O_5NaP$ requires 537.1991).

EXAMPLE 13

(1R,cis)-4-(6-Amino-9H-purin-9-yl)-2-cyclopentene-1-methanol O-[phenyl (2,2-dimethylpropoxy)-L-alaninyl]phosphoramidate Synthesis according to standard procedure 1. Title compound isolated as a brittle white foam (66%); $\delta_P$ 3.89, 4.18; $\delta_H$ 0.94 (9H, d), 1.41 (3H, m), 1.73 (1H, m), 2.89 (1H, m), 3.23 (1H, m), 3.83 (2H, m), 4.14 (4H, m), 5.77 (1H, m), 5.98 (1H, m), 6.20 (3H, m), 7.18 (2H, m), 7.32 (3H, m), 7.88, 7.94 (1H, s), 8.38 (1H, s); m/z (ES+) 551.2145 (MH$^+$, $C_{25}H_{33}N_6O_5NaP$ requires 551.2148).

EXAMPLE 14

(1R,cis)-4-(6-Amino-9H-purin-9-yl)-2-cyclopentene-1-methanol O-(phenyl cyclopropyl methoxy-L-alaninyl)phosphoramidate Synthesis according to standard procedure 1. Title compound isolated as a brittle white foam (59%); $\delta_P$ 3.99, 4.21; $\delta_H$ 0.14 (2H, m), 0.45 (2H, m), 0.99 (1H, m), 1.28 (3H, m), 1.61 (1H, m), 2.76 (1H, m), 3.10 (1H, m), 3.84 (2H, m), 4.06 (2H, m), 4.50 (1H, m), 5.64 (1H, m), 5.85 (1H, m), 6.06 (1H, m), 6.42 (2H, br s), 7.13 (5H, m), 7.77,7.80 (1H, s),8.27 (1H, s); m/z (ES+) 535.1834 (MH$^+$, $C_{24}H_{29}N_6O_5NaP$ requires 535.1835).

EXAMPLE 15

(1R,cis)-4-(6-Amino-9H-purin-9-yl)-2-cyclopentene-1-methanol O-(phenyl methoxy-L-leucinyl)phosphoramidate Synthesis according to standard procedure 1. Title compound isolated as a brittle white foam (79%); $\delta_P$ 4.14, 4.37; $\delta_H$ 0.78 (6H, m), 1.39 (2H, m), 1.58 (2H, m), 2.77 (1H, m), 3.10 (1H, m), 3.56,3.59 (3H, s), 4.02 (4H, m), 5.65 (1H, m), 5.86 (1H, m), 6.00 (1H, m), 6.26 (2H, br s), 7.06 (2H, m), 7.21 (3H, m), 7.77, 7.84 (1H, s), 8.28 (1H, s); m/z (ES+) 537.2000 (MH$^+$, $C_{24}H_{31}N_6O_5NaP$ requires 537.1991).

EXAMPLE 16

(1R,cis)-4-(6-Amino-9H-purin-9-yl)-2-cyclopentene-1-methanol O-[phenyl methoxy-L-(O-methyl-tyrosinyl)]phosphoramidate Synthesis according to standard procedure 1. Title compound isolated as a brittle white foam (89%); $\delta_P$ 4.07; $\delta_H$ 1.62 (1H, m), 2.81 (1H, m), 2.93 (2H, m), 3.12 (1H, m), 3.64, 3.68 (3H, s), 3.74 (3H, m), 4.09 (3H, m), 4.47 (1H, m), 5.73 (1H, m), 5.94 (1H, m), 6.11 (1H, m), 6.43 (2H, br s), 6.75 (2H, d), 6.98 (2H, d), 7.16 (3H, m), 7.27 (2H, m), 7.83, 7.85 (1H, s), 8.36, 8.37 (1H, s).

EXAMPLE 17

(1R,cis)-4-(6-Amino-9H-purin-9-yl)-2-cyclopentene-1-methanol O-(phenyl methoxy-D-phenylalaninyl)phosphoramidate Synthesis according to standard procedure 1. Title compound isolated as a brittle white foam (24%), $\delta_P$ 3.92, 4.04; $\delta_H$ 1.7 (1H, m), 2.8 (1H, m), 3.1 (1H, m), 3.2 (1H, m), 3.7 (3H, d), 4.1 (2H, m), 4.6 (1H, q), 5.7 (1H, m), 5.9 (1H, m), 6.1 (1H, m), 6.5 (2H, d), 7.2 (10H, m), 7.85 (1H, d), 8.4 (1H, d).

EXAMPLE 18

(1R,cis)-4-(6-Amino-9H-purin-9-yl)-2-cyclopentene-1-methanol O-(phenyl methoxy-D-leucinyl) phosphoramidate Synthesis according to standard procedure 1. Title compound isolated as a brittle white foam (28%), $\delta_P$ 4.27, 4.36; $\delta_H$ 0.8 (6H, m), 1.5 (2H, m), 5.9 (1H, m), 6.05 (1H, m), 6.55 (2H, s),7.2 (5H, m), 7.8 (1H, d), 8.23 (1H, d).

EXAMPLE 19

(1R,cis)-4-(6-Amino-9H-purin-9-yl)-2-cyclopentene-1-methanol O-(phenyl methoxy-D-tryptophanyl)phosphoramidate (diastereomeric mixture)

Synthesis according to standard procedure 1. Elution from a silica gel column with 5% methanol in methylene chloride gave a 1.15:1 mixture of high:low $R_f$ isomers (from $^{31}$P-NMR), isolated as a brittle white foam (23%); $\delta_P$ 4.13, 4.23; $\delta_H$ 1.5 (1H, m), 2.65 (1H, m), 3.2 (2H, m), 3.62 (3H, d), 3.95 (2H, m), 4.35 (1H, m), 5.67 (1H, m), 5.9 (1H, m), 6.0 (1H, m), 6.4 (2H, s), 7.2 (9H, m), 7.5 (1H, d), 7.73 (1H, s), 8.35 (1H, s), 9.05 (1H, s).

EXAMPLE 20

(1R,cis)-4-(6-Amino-9H-purin-9-yl)-2-cyclopentene-1-methanol O-(phenyl methoxy-D-tryptophanyl)phosphoramidate (single diastereomer)

Synthesis according to standard procedure 1. Elution from a silica gel column with 5% methanol in methylene chloride gave initial fractions containing the pure higher $R_f$ isomer of the mixture described in Example 19 (from $^{31}$P-NMR), isolated as a brittle white foam (34%); $\delta_P$ 4.02; $\delta_H$ 1.5 (1H, m), 2.7 (1H, m), 3.2 (2H, m), 3.6 (3H, d), 4 (2H, m), 4.3 (1H, m), 5.7 (1H, m), 5.85 (1H, m), 6 (1H, m), 6.5 (2H, s), 7.3 (9H, m), 7.5 (1H, d), 7.8 (1H, s),8.4 (1H, s), 9.2 (1H, s).

EXAMPLE 21

(1R,cis)-4-(6-Amino-9H-purin-9-yl)-2-cyclopentene-1-methanol O-(phenyl methoxy-D-valinyl) phosphoramidate Synthesis according to standard procedure 1. Title compound isolated as a brittle white foam (26%), $\delta_P$ 4.76, 4.85; $\delta_H$ 0.9 (6H, m), 1.8 (1H, m), 2.1 (1H, m), 3.25 (1H, m), 3.7 (3H, d), 3.9 (1H, m), 4.2 (2H, m), 5.8 (1H, m), 6 (1H, m), 6.2 (1H, m), 6.3 (2H, s), 7.25 (5H, m), 7.9 (1H, d), 8.4 (1H, s).

EXAMPLE 22

(1R,cis)-4-(6-Amino-9H-purin-9-yl)-2-cyclopentene-1-methanol O-(phenyl dimethoxy-D-aspartyl) phosphoramidate Synthesis according to standard procedure 1 Title compound isolated as a brittle white foam (28%), $\delta_P$ 3.79, 4.24; $\delta_H$ 1.7 (1H, m), 2.8 (3H, m), 3.1 (1H, m), 3.6 (3H, d), 3.7 (3H, d), 4.1 (2H, m), 4.4 (1H, m), 5.5 (1H, m), 5.9 (1H, m), 6.1 (1H, m), 6.3 (2H, s), 7.15 (5H, m), 7.8 (1H, d),8.3 (1H, d)

EXAMPLE 23

(1R,cis)-4-(6-Amino-9H-purin-9-yl)-2-cyclopentene-1-methanol O-(phenyl methoxy-L-prolinyl) phosphoramidate Synthesis according to standard procedure 1. Title compound isolated as a brittle white foam (19%); $\delta_P$ 2.89, 3.04; $\delta_H$ 1.68–2.19 (5H, br m), 2.94 (1H, m), 3.32 (2H, m), 3.42 (1H, m), 3.61,3.74 (3H, s), 4.12, 4.30 (m, 5'-H), 5.70 (2H, br s) 5.81 (1H, m), 5.98 (1H, m), 6.19, 6.25 (1H, m), 7.21 (2H, m), 7.35 (3H, m), 7.88, 8.02 (1H, s), 8.43 (1H, s).

EXAMPLE 24

(1R,cis)-4-(6-Amino-9H-purin-9-yl)-2-cyclopentene-1-methanol O-(phenyl methoxy-L-isoleucinyl) phosphoramidate Synthesis according to standard procedure 1. Title compound isolated as a brittle white foam (45%); $\delta_P$ 4.55, 4.72; $\delta_H$ 0.92 (6H, m), 1.16 (1H, m), 1.42 (1H, m), 1.77 (2H, m), 2.99 (1H, m), 3.22 (1H, m), 3.62, 3.66 (3H, s), 3.84 (2H, m), 4.22 (2H, m), 5.74 (1H, m), 5.99 (3H, m), 6.17 (1H, m), 7.11 (2H), 7.29 (3H, m), 7.86, 7.92 (1H, s), 8.36 (1H, s).

EXAMPLE 25

(1R,cis)-4-(6-Amino-9H-purin-9-yl)-2-cyclopentene-1-methanol O-(phenyl methoxy-L-norvalinyl) phosphoramidate Synthesis according to standard procedure 1. Title compound isolated as a brittle white foam (73%); $\delta_P$ 4.10, 4.35; $\delta_H$ 0.88 (3H, t, J 8.4), 1.32 (2H, m), 1.71 (3H, m), 2.91 (1H, m), 3.20 (1H, m), 3.65, 3.68 (3H, s), 3.87 (1H, m), 4.03 (2H, m), 4.19 (1H, m), 5.74 (1H, m), 5.93 (1H, m), 6.05 (2H, br s), 6.13 (1H, m), 7.14 (2H, m), 7.28 (3H, m), 7.83, 7.90 (1H, s), 8.34 (1H, s).

EXAMPLE 26

(1R,cis)-4-(6-Amino-9H-purin-9-yl)-2-cyclopentene-1-methanol O-(phenyl i-propoxy-L-phenylalaninyl)phosphoramidate Synthesis according to standard procedure 1. Title compound isolated as a brittle white foam (76%); $\delta_P$ 3.97; $\delta_H$ 1.20 (6H, m), 1.66 (2H, m), 2.82 (1H, m), 2.98 (2H, m), 3.11

(1H, m), 3.79–4.06 (4H, br m), 4.99 (1H, m), 5.72 (1H, m), 5.96 (1H, m), 6.08 (3H, m), 7.23 (10H, m), 7.87 (1H, s), 8.34 (1H, s).

EXAMPLE 27

(1R,cis)-4-(6-Amino-9H-purin-9-yl)-2-cyclopentene-1-methanol O-(phenyl tert-butoxy-L-phenylalaninyl)phosphoramidate Synthesis according to standard procedure 1. Title compound isolated as a brittle white foam (51%); $\delta_P$ 4.14, 4.09; $\delta_H$ 1.31, 1.34 (9H, s), 1.56 (1H, m), 2.75 (1H, m), 2.90 (2H, m), 3.20 (1H, m), 3.94 (4H, m), 5.63 (1H, m), 5.86 (1H, m), 6.02 (3H, m), 7.13 (10H, m), 7.73 (1H, s), 8.29 (1H, s).

EXAMPLE 28

(1R,cis)-4-(6-Amino-9H-purin-9-yl)-2-cyclopentene-1-methanol O-[phenyl (2,2-dimethylpropoxy)-L-phenylalaninyl]phosphoramidate Synthesis according to standard procedure 1. Title compound isolated as a brittle white foam (23%); $\delta_P$ 3.94, 3.99; $\delta_H$ 0.85, 0.92 (9H, s), 1.62 (1H, m), 2.80 (1H, m), 3.03 (2H, m), 3.20 (1H, m), 3.79 (3H, m), 4.02 (2H, m), 4.29 (1H, m), 5.73 (1H, m), 5.92 (1H, m), 6.02 (2H, brs), 6.09 (1H, m), 7.18 (10H, m), 7.81, 7.83 (1H, s), 8.36, 8.37 (1H, s).

EXAMPLE 29

(1R,cis)-4-(6-Amino-9H-purin-9-yl)-2-cyclopentene-1-methanol O-(phenyl benzyloxy-L-phenylalaninyl)phosphoramidate Synthesis according to standard procedure 1. Title compound isolated as a brittle white foam (53%); $\delta_P$ 3.84, 3.90; $\delta_H$ 1.56 (1H, m), 2.81 (1H, m), 3.02 (3H, m), 3.92 (3H, m), 4.27 (1H, m), 5.11 (2H, m) 5.69 (1H, m), 5.85 (1H, m), 6.03 (3H, br s), 6.94 (2H, m), 7.13 (13H, m), 7.77, 7.78, 7.80 (1H, s), 8.34 (1H, s).

EXAMPLE 30

(1R,cis)-4-(6-Amino-9H-purin-9-yl)-2-cyclopentene-1-methanol O-[(2-carbomethoxy)phenyl methoxy-L-alaninyl]phosphoramidate Synthesis according to standard procedure 3. Title compound isolated as a brittle white foam (39%); $\delta_P$ 3.95, 4.05; $\delta_H$ 1.28 (6H, m), 1.69 (1H, m), 2.80 (1H, m), 3.15 (1H, m), 3.52, 3.60 (3H, s), 4.18 (5H, m), 5.70 (1H, m), 5.88 (1H, m), 7.16 (1H, m), 7.44 (2H, m), 7.80 (1H, m), 7.87, 7.92 (1H, s), 8.28 (1H, s); MS (E/I) 567.1722 (calc. 567.1733).

EXAMPLE 31

(1R,cis)-4-(6-Amino-9H-purin-9-yl)-2-cyclopentene-1-methanol O-[4-(3-oxo-3-phenylpropenylphenyl methoxy-L-alaninyl]phosphoramidate Synthesis according to standard procedure 1. Title compound isolated as a brittle white foam (74%); $\delta_P$ 3.68, 3.97; $\delta_H$ 1.40 (3H, m), 1.78 (1H, m), 2.93 (1H, m), 3.25 (1H, br, s), 3.75 (3H, s), 4.27 (3H, m), 5.78 (1H, m), 6.10 (1H, m), 6.19 (1H, m), 7.25 (1H, m), 7.32 (2H, m), 7.58 (4H, m), 7.90 (1H, s), 8.05 (2H, s), 8.50 (1H, s); MS (E/I) 625.1956 (calc. 625.1940).

EXAMPLE 32

(1R,cis)-4-(6-Amino-9H-purin-9-yl)-2-cyclopentene-1-methanol O-(phenyl methoxy glycinyl)phosphoramidate Synthesis according to standard procedure 1. Title compound isolated as a brittle white foam (38%); $\delta_P$ 4.51; $\delta_H$ 1.72 (1H, m), 2.82 (1H, m), 3.20 (1H, m), 3.70 (3H, s), 4.00 (2H, m), 4.20 (2H, m) 5.68 (1H, m), 5.90 (1H, m), 6.15 (1H, m), 7.20 (5H, m), 7.99 (1H, s), 8.31 (1H, s); MS (EI) 481.1373 (calc. 481.1365).

EXAMPLE 33

(1R,cis)-4-(6-Amino-9H-purin-9-yl)-2-cyclopentene-1-methanol O-(phenyl methoxy-L-valinyl) phosphoramidate Synthesis according to standard procedure 1. Title compound isolated as a brittle white foam (86%); $\delta_P$ 4.64, 4.84; $\delta_H$ 0.83 (6H, m), 1.65 (1H, m), 1.95 (1H, m), 2.82 (1H, m), 3.15 (1H, m), 3.60, 3.65 (3H, s), 3.78 (1H, m), 4.11 (2H, m), 5.68 (1H, m), 5.89 (1H, m), 6.12 (1H, m), 7.10 (2H, m), 7.22 (3H, m), 7.84, 7.92 (1H, s), 8.29 (1H, s); MS (EI) 523.1855 (calc. 523.1835).

EXAMPLE 34

(1R,cis)-4-(6-Amino-9H-purin-9-yl)-2-cyclopentene-1-methanol O-(phenyl methoxy-L-methioninyl) phosphoramidate Synthesis according to standard procedure 1. Title compound isolated as a brittle white foam (96%); $\delta_P$ 3.79, 4.19; $\delta_H$ 1.70 (1H, m), 1.85 (2H, m), 1.97 (3H, s), 2.39 (2H, t), 2.81 (1H, m), 3.15 (1H, m), 3.64, 3.67 (3H, s), 3.91 (1H, m), 4.13 (2H, m), 5.68 (1H, m), 5.89 (1H, m), 6.12 (1H, m), 7.12 (2H, m), 7.28 (3H, m), 7.90, 8.00 (1H, s),8.29 (1H, s); MS (E/I) 555.1567 (calc. 555.1555).

EXAMPLE 35

(1R,cis)-4-(6-Amino-9H-purin-9-yl)-2-cyclopentene-1-methanol O-(phenyl ethoxy-α,α-dimethylglycinyl)phosphoramidate Synthesis according to standard procedure 1. Title compound isolated as a brittle white foam (91%); $\delta_P$ 2.51; $\delta_H$ 1.30 (3H, t), 1.57 (6H, m), 1.73 (1H, m), 2.88 (1H, m), 3.22 (1H, m), 4.19 (4H, m), 5.74 (1H, m), 5.95 (1H, m), 6.19 (1H, m), 7.23 (5H, m), 7.92, 7.96 (1H, s), 8.35 (1H, s).

EXAMPLE 36

(1R,cis)-4-(6-Amino-9H-purin-9-yl)-2-cyclopentene-1-methanol O-(phenyl isopropoxy-α,α-dimethylglycinyl)phosphoramidate Synthesis according to standard procedure 1. Title compound isolated as a brittle white foam (21%); $\delta_P$ 2.56; $\delta_H$ 1.30 (6H, m), 1.58 (6H, m), 1.78 (1H, m), 2.90 (1H, m), 3.24 (1H, m), 4.08 (1H, m), 4.20 (2H, m), 5.07 (1H, m), 5.65 (2H, br, s), 6.00 (1H, m), 6.20 (1H, m), 7.26 (5H, m), 7.83, 7.89 (1H, s), 8.43 (1H, s).

EXAMPLE 37

(1R,cis)-4-(6-Amino-9H-purin-9-yl)-2-cyclopentene-1-methanol O-[phenyl (2,2-dimethylpropoxy-α,α-dimethylglycinyl]phosphoramidate Synthesis according to standard procedure 2. Title compound isolated as a brittle white foam (38%); $\delta_P$ 2.42, 2.44; $\delta_H$ 0.99 (9H, s), 1.61 (6H, dd), 1.74 (1H, m), 2.90 (1H, m), 3.23 (1H, m), 3.86 (2H, s), 4.20 (2H, m), 5.78 (1H, m), 6.00 (1H, m), 6.20 (1H, m), 7.28 (5H, m), 7.86, 7.92 (1H, s), 8.40 (1H, s).

EXAMPLE 38

(1R,cis)-4-(6-Amino-9H-purin-9-yl)-2-cyclopentene-1-methanol O-(phenyl methoxy cyclopentaneglycinyl)phosphoramidate Synthesis according to standard procedure 1. Title compound isolated as a brittle white foam (54%); $\delta_P$ 2.94; $\delta_H$ 1.67 (1H, m), 2.04 (8H, m), 2.91 (1H, m), 3.24 (1H, m), 3.75 (3H, s), 4.25 (2H, m), 5.80 (1H, m), 6.02 (1H, m), 6.22 (1H, m), 7.25 (5H, m), 7.90, 8.00 (1H, s), 8.45 (1H, s); MS (EI) 535.1816 (calc. 535.1835).

EXAMPLE 39

(1R,cis)-4-(6-Amino-9H-purin-9-yl)-2-cyclopentene-1-methanol O-(phenyl methoxy cyclohexaneglycinyl)phosphoramidate Synthesis according to standard procedure 1. Title compound isolated as a brittle white foam (44%); $\delta_P$ 2.88; $\delta_H$ 1.64 (10H, m), 1.71 (1H, m), 2.85 (1H, m), 3.20 (1H, m), 3.71 (3H, s), 4.19 (2H, m), 5.76 (1H, m), 5.98 (1H, m), 6.17 (1H, m), 7.25 (5H, m), 7.85, 7.95 (1H, s), 8.42 (1H, s); MS (EI) 549.2008 (calc. 549.1991).

EXAMPLE 40

(1R,cis)-4-(6-Amino-9H-purin-9-yl)-2-cyclopentene-1-methanol O-(phenyl dimethoxy-L-aspartyl)phosphoramidate Synthesis according to standard procedure 2. Title compound isolated as a brittle white foam (34%); $\delta_P$ 3.78, 4.38; $\delta_H$ 1.74 (1H, m), 2.85 (1H, m), 3.22 (1H, m), 3.50 (2H, s), 3.65 (3H, s), 3.75 (3H, s), 4.13 (1H, m), 4.26 (2H, m), 5.71 (1H, m), 5.92 (1H, m), 6.23 (1H, m), 7.16 (5H, m), 8.00 (1H, m), 8.13, 8.21 (1H, s).

EXAMPLE 41

(1R,cis)-4-(6-Amino-9H-purin-9-yl)-2-cyclopentene-1-methanol O-[(4-chlorophenyl) methoxy-L-alaninyl]phosphoramidate Synthesis according to standard procedure 1. Title compound isolated as a brittle white foam (28%), $\delta_P$ 3.88, 4.16; $\delta_H$ [CDCl$_3$] 1.3 (3H, m), 1.7 (1H, m), 2.9 (1H, m), 3.2 (1H, m), 3.7 (3H, d), 4.2 (2H, m), 5.7 (1H, m), 6 (1H, m), 6.2 (1H, m), 7.3 (4H, m), 7.95 (1H, d), 8.4 (1H, d).

EXAMPLE 42

(1R,cis)-4-(6-Amino-9H-purin-9-yl)-2-cyclopentene-1-methanol O-(L-(methylamino)alaninyl)phosphoramidate (1R,cis)-4-(6-Amino-9H-purin-9-yl)-2-cyclopentene-1-methanol O-[phenyl(methoxy)-L-alaninyl]phosphoramidate (Example 2, 60 mg, 0.127 mmoles) was suspended in solution of 40% methylamine (2 mL) and stirred at room temperature for 4 hours. The volatiles were removed by spin evaporation in vacuo and the residue was dissolved in water (20 mL), extracted with dichloromethane (2×20 mL) and purified by anion exchange chromatography on a Sep-Pak Vac 35cc Accell™ Plus QMA cartridge (Waters Corp., P/N WAT054725) (HCO$_3^-$ form) with an aqueous ammonium bicarbonate buffer (0–0.5 M gradient, 1 L). The appropriate fractions were combined and the volatiles were removed by spin evaporation in vacuo. The residue was twice dissolved in deionized water and spin evaporated in vacuo to give the title compound as an ammonium salt. This salt was dissolved in deionized water and passed through a Sep-Pak™ Vac 20cc Accell™ Plus CM cartridge (Waters Corp., P/N WAT054675) (Na$^+$ form) using deionized water. Lyophilization of the appropriate fractions left the title compound sodium salt as a white solid (26 mg, 520%); $^1$H-NMR (D2O) δ 7.92 (s, 1H), 7.91 (s, 1H), 6.09–6.15 (m, 1H), 5.83–5.88 (m, 1H), 5.30–5.40 (m, 1H), 3.62 (t, J=5.3 Hz, 1H), 3.28–3.48 (m, 2H), 2.92–3.04 (bm, 1H), 2.58–2.71 (m, 1H), 2.44–2.51 (m, 3H), 1.36–1.46 (m, 1H), 1.01 (d, J=6.8 Hz, 3H); $^{31}$P-NMR (D$_2$O) 6.55. Mass spectrum (ES$^-$) m/e 394 (M–H).

EXAMPLE 43

(1R,cis)-4-(6-Amino-9H-purin-9-yl)-2-cyclopentene-1-methanol O-(phenyl)phosphate This compound was prepared in an analogous manner to Example 42 with the replacement of phosphoryl chloride by phenyl dichlorophosphate. Removal of the volatiles by evaporation in vacuo gave the ammonium salt of the title molecule as a hygroscopic solid (99 mg, 570%); $^1$H-NMR (D2O) δ 7.92 (s, 1H), 7.75 (s, 1H), 6.82–6.92 (m, 2H), 6.62–6.76 (m, 3H), 6.08–6.16 (m, 1H), 5.81–5.88 (m, 1H), 5.16–5.25 (m, 1H), 3.79–3.88 (m, 1H), 3.61–3.72 (m, 1H), 3.2.95–3.3.06 (bm, 1H), 2.42–2.58 (m, 1H), 1.18–1.30 (m, 1H); $^{31}$P-NMR (D$_2$O) −4.56 (m, 1P), Mass spectrum (ES$^-$) m/e 386 (M–H).

EXAMPLE 44

(1R,cis)-4-(6-Amino-9H-purin-9-yl)-2-cyclopentene-1-methanol O-monophosphate (1R,cis)-4-(6-Amino-9H-purin-9-yl)-2-cyclopentene-1-methanol (Example 1, 200 mg, 0.865 mmol) was dissolved in 1,3-dimethyl-3,4,5,6-tetrahydro-2(1H)-pyrimidinone (2 mL). Phosphoryl chloride (0.24 mL, 0.26 mmol) was added to the stirred, cooled (0° C.) solution. After 1 minute, 1.0 M sodium hydrogen carbonate (3.3 mL, 3.3 mmol) was added and stirring was continued at 0° C. for 30 minutes and then at 25° C. for 1 hour. The reaction solution was diluted to 125 mL with deionized water and applied to a 1.1×7.0 cm DEAE Sepahadex A25 (Aldrich) ion exchange chromatography column which had been washed with 1.0 M ammonium bicarbonate buffer and then equilibrated with deionized water. The title compund was eluted with a 0 to 0.5 M gradient (2 L) of ammonium bicarbonate. The appropriate fractions were combined and the volatiles removed by evaporation in vacuo. The residue was redissolved in deionized water (20 mL) and evaporated in vacuo three times. Lyophylization of the residue from water gave the ammonium salt of the title compound (270 mg, 90% as mono ammonium salt, monohydrate); $^1$H-NMR (D$_2$O) δ 8.10 (S, 2H), 6.14–6.20 (m, 1H), 5.84–5.90 (m, 1H), 5.48–5.58 (m, 1H), 3.71–3.86 (m, 2H), 3.02–3.14 (br m, 1H), 2.66–2.80 (m, 1H), 1.56–1.66 (m, 1H); $^{31}$P-NMR (D$_2$O) 0.62. Mass spectrum (ES$^-$) m/e 310 (M–H).

EXAMPLE 45

(1R,cis)-4-(6-Amino-9H-purin-9-yl)-2-cyclopentene-1-methanol O-diphosphate

The title molecule was prepared by a modification of the method of Broom (Mishra, N. C. and Broom, A. D., J. Chem. Soc., Chem. Commun., 1991, 1276). (1R,cis)-4-(6-Amino-9H-purin-9-yl)-2-cyclopentene-1-methanol (Example 1, 231 mg, 1.0 mmol) was dissolved in trimethyl phosphate (5 mL). Phosphoryl chloride (0.27 mL, 3.0 mmol) was added to the stirred, cooled (0° C.) solution. After 3 hours, a solution of 86% phosphoric acid (1.14 g, 10 mmol) and tri-n-butylamine (2.4 mL, 10 mmol) in dimethyformamide (15 mL) was added to the cold (0° C.) stirring solution, followed immediately by tri-n-butylamine (3 mL). After 1 minute, 1 M triethylammonium hydrogen carbonate buffer (100 mL) was added and stirring was continued for 30 minutes. The reaction solution was diluted to 3 L with deionized water and applied to a 1.1×7.0 cm DEAE Sepahadex A25 (Aldrich) ion exchange chromatography column which had been washed with 1.0 M ammonium bicarbonate and preequilibrated with deionized water. The title compound was eluted with a 0 to 0.5 M gradient (4 L) of ammonium bicarbonate. The appropriate fractions were combined and the volatiles removed by evaporation in vacuo, redissolved in water and evaporated again to give the ammonium salt of the title compound (0.37 mmol, 37%); UV (0.1 M HCl)λ max=260 nm. UV purity (254 nm detection) was 100% by analytical strong anion exchange HPLC (Whatman Partisil 5, SAX RAC II, 0.05 M to 0.95 M gradient with ammonium phosphate buffer (pH 5.5), 5% methanol). $^1$H-NMR (D$_2$O) δ 8.06 (s, 1H), 8.05 (s, 1H), 6.13–6.21 (m, 1H), 5.82–5.88 (m, 1H), 5.45–5.53 (m, 1H), 3.76–3.90 (m, 2H), 3.02–3.16 (br m, 1H), 2.64–2.78 (m, 1H), 1.52–1.64 (m, 1H); $^{31}$P-NMR (D$_2$O) −9.90 (d, 1P, J=20.3 Hz), −10.84 (d, 1P, J=20.3). Mass spectrum (ES$^-$) m/e 390 (M–H).

EXAMPLE 46

(1R,cis)-4-(6-Amino-9H-purin-9-yl)-2-cyclopentene-1-methanol O-triphosphate

Continued elution of the column described in Example 45 gave, on evaporation, the ammonium salt of the title compound (11.4 mmoles, 11.4%). UV (0.1 M HCl) λ max=260 nm. UV purity (254 nm detection) was 98% by analytical strong anion exchange HPLC (Whatman Partisil 5, SAX RAC II, 0.05 M to 0.95 M gradient with ammonium phosphate buffer (pH 5.5), 5% methanol). $^1$H-NMR (D$_2$O) δ 8.10 (s, 2H), 6.18–6.23 (m, 1H), 5.84–5.90 (m, 1H), 5.41–5.59 (m, 1H), 3.82–3.98 (m, 2H), 3.04–3.18 (br m, 1H), 2.54–2.66 (m, 1H), 1.52–1.64 (m, 1H); $^{31}$P-NMR (D$_2$O) −8.38 (m, 1P), 10.85 (d, 1P, J=19.3 Hz), −22.73 (m, 1P). Mass spectrum (ES$^-$) m/e 470 (M–H).

EXAMPLE 47

Anti-HIV Activity

Compounds according to the invention were tested for anti-HIV activity in MT$_4$ cells according to the method described by Averett, D. R., J. Virol. Methods, 23, 1989, 263–276. Activity of the compounds was in the range of IC$_{50}$ 0.009–2.1 μM.

EXAMPLE 48

Anti-Hepatitis B Virus Activity

Compounds were tested for anti-Hepatitis B Virus activity according to the method described by Jansen, R. et al., Antimicrobial Agents and Chemotherapy, Vol. 37, No. 3, pp. 441–447, 1993, and results are shown in the table below. IC$_{50}$ values of the compounds according to the invention demonstrated improved activity by as much as 500-fold over that of the corresponding nucleoside analog, (1R,cis)-4-(6-amino-9H-purin-9-yl)-2-cyclopentene-1-methanol.

| Example | IC$_{50}$ (mM) vs. HBV | Selectivity Index |
|---|---|---|
| 2 | 0.018 | 1300 |
| 4 | 0.033 | 6100 |
| 5 | 0.0075 | 1250 |
| 6 | 0.0045 | 2000 |
| 7 | 0.0032 | 5000 |
| 8 | 0.11 | >1800 |
| 9 | 0.002 | 5000 |
| 1 | 0.98 | >200 |

EXAMPLE 49

Tablet Formulation

The following formulations A, B and C are prepared by wet granulation of the ingredients with a solution of povidone, followed by addition of magnesium stearate and compression.

| | mg/tablet |
|---|---|
| Formulation A | |
| Active Ingredient | 250 |
| Lactose B.P. | 210 |
| Povidone B.P. | 15 |
| Sodium Starch Glycollate | 20 |
| Magnesium Stearate | 5 |
| | 500 |
| Formulation B | |
| Active Ingredient | 250 |
| Lactose B.P. | 150 |
| Avicel PH 101 | 60 |
| Povidone B.P. | 15 |
| Sodium Starch Glycollate | 20 |
| Magnesium Stearate | 5 |
| | 500 |

-continued

| | mg/tablet |
|---|---|
| Formulation C | |
| Active Ingredient | 250 |
| Lactose B.P. | 200 |
| Starch | 50 |
| Povidone | 5 |
| Magnesium Stearate | 4 |
| | 359 |

The following formulations, D and E, are prepared by direct compression of the admixed ingredients. The lactose in formulation E is of the direct compression type (Dairy Crest-"Zeparox").

| | mg/tablet |
|---|---|
| Formulation D | |
| Active Ingredient | 250 |
| Pregelatinized Starch NF15 | 150 |
| | 400 |
| Formulation E | |
| Active Ingredient | 250 |
| Lactose B.P. | 150 |
| Avicel | 100 |
| | 500 |

Formulation F (Controlled Release Formulation)

The formulation is prepared by wet granulation of the ingredients with a solution of povidone followed by the addition of magnesium stearate and compression.

| | mg/tablet |
|---|---|
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |
| | 700 |

Drug release takes place over a period of about 6–8 hours and is complete after 12 hours.

EXAMPLE 50

Capsule Formulations

Formulation A

A capsule formulation is prepared by admixing the ingredients of formulation D in Example 49 above and filling into a two-part hard gelatin capsule. Formulation B (infra) is prepared in a similar manner.

| | mg/capsule |
|---|---|
| Formulation B | |
| Active Ingredient | 250 |
| Lactose B.P. | 143 |
| Sodium Starch Glycollate | 25 |
| Magnesium Stearate | 2 |
| | 420 |
| Formulation C | |
| Active Ingredient | 250 |
| Macrogel 4000 B.P. | 350 |
| | 600 |

Capsules of formulation C are prepared by melting the Macrogel 4000 B.P., dispersing the active ingredient in the melt and filling the melt into a two-part hard gelatin capsule.

| Formulation D | mg/capsule |
|---|---|
| Active Ingredient | 250 |
| Lecithin | 100 |
| Arachis Oil | 100 |
| | 450 |

Capsules of formulation D are prepared by dispersing the active ingredient in the lecithin and arachis oil and filling the dispersion into soft, elastic gelatin capsules.

| Formulation E | mg/capsule |
|---|---|
| Active Ingredient | 150.0 |
| Vitamin E TPGS | 400.0 |
| Polyethylene Glycol 400 NF | 200.5 |
| Propylene Glycol USP | 39.5 |

Four (4) kilograms (kg) of Vitamin E TPGS (obtained from Eastman Chemical Co.) was heated at 50° C. until liquefied. To the liquefied Vitamin E TPGS, 2.005 kg of polyethylene glycol 400 (PEG400) (low aldehyde, <10 ppm, obtained from Union Carbide or Dow Chemical Co.) heated to 50° C. was added and mixed until a homogeneous solution was formed. The resultant solution was heated to 65° C. 1.5 kg of active ingredient was dissolved in the liquefied solution of Vitamin E TPGS and PEG 400. 0.395 kg of propylene glycol at room temperature was added and mixed until a homogenous solution was formed. The solution was cooled to 28–35° C. The solution was then degassed. The mixture was preferably encapsulated at 28–35° C. at a fill weight equivalent to 150 mg of volatiles-free compound, into Size 12 oblong, white opaque soft gelatin capsules using a capsule filling machine. The capsule shells were dried to a constant fill moisture of 3–6% water and a shell hardness of 7–10 Newtons, and placed in a suitable container.

Formulation F (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

|     |                            | mg/capsule |
| --- | -------------------------- | ---------- |
| (a) | Active Ingredient          | 250        |
| (b) | Microcrystalline Cellulose | 125        |
| (c) | Lactose B.P.               | 125        |
| (d) | Ethyl Cellulose            | 13         |
|     |                            | 513        |

EXAMPLE 51

Injectable Formulation

| Formulation A | mg |
| --- | --- |
| Active Ingredient | 200 |
| Hydrochloric Acid Solution 0.1M or Sodium Hydroxide Solution 0.1M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

| Formulation B | |
| --- | --- |
| Active Ingredient | 125 mg |
| Sterile, Pyrogen-free, pH 7 Phosphate Buffer, q.s. to | 25 ml |

EXAMPLE 52

Intramuscular Injection

| Active Ingredient | 200 mg |
| --- | --- |
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 53

Syrup

| Active Ingredient | 250 mg |
| --- | --- |
| Sorbitol Solution | 1.50 g |

| -continued | |
| --- | --- |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

EXAMPLE 54

Suppository

|  | mg/capsule suppository |
| --- | --- |
| Active Ingredient | 250 |
| Hard Fat, B.P. (Witepsol H15-Dynamit Nobel) | 1770 |
|  | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 45° C. At a temperature of 38° C. to 40° C., 2.02 g of the mixture is filled into suitable, 2 ml plastic molds. The suppositories are allowed to cool to room temperature.

EXAMPLE 55

Pessaries

|  | mg/pessary |
| --- | --- |
| Active Ingredient | 250 |
| Anhydrate Dextrose | 380 |
| Potato Starch | 363 |
| Magnesium Stearate | 7 |
|  | 1000 |

The above ingredients are mixed directly.

EXAMPLE 56

Acid Stability

Compounds according to the invention were tested for their stability towards acid-mediated hydrolytic decomposition employing a test designed to simulate stomach conditions. Each compound was incubated at an initial concentration of 0.3 mg/ml in dilute hydrochloric acid at pH 1 at 37° C. HPLC was run immediately for t=0 and at intervals up to approximately 24 hours. The half-life of title compound from Example 7 was 76 hours under these conditions. Comparative phosphoramidates of 2',3'-dideoxy-adenosine (Compound 1093) and 2',3'-didehydro-2',3'-dideoxy-adenosine (Compound 1001), described in PCT/GB96/00580, were significantly less stable at pH1. Compound 1001 was completely decomposed in <1 minute at pH 1 (25° C.). Compound 1093 was completely decomposed after 13 hours at pH 1 (25° C.).

EXAMPLE 57

Biological Stability

Title compound of Example 7 and phosphoramidates of 2',3'-dideoxy-adenosine (Compound 1093) and 2',3'-didehydro-2',3'-dideoxy-adenosine (Compound 1001), described in PCT/GB96/00580, were tested for their stability towards biological decomposition. Each compound was incubated in normal heparized human plasma at 37° C. At selected time points duplicate samples were removed and deproteinated by acetonitrile extraction. Drug concentrations were then determined by LC/MS/MS analysis using standard methods. Half-lives were calculated and are shown in the table below.

| Compound | Half-life (hours) |
| --- | --- |
| Example 7 | 53 |
| 1001 | 4.6 |
| 1093 | 4.2 |

The half-life in human plasma of compound of the present invention is more than 10-fold greater than those of compounds 1001 and 1093.

The invention claimed is:

1. A compound of formula (I)

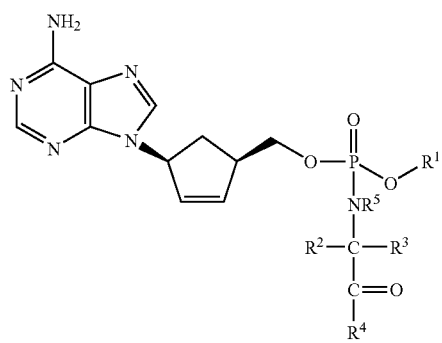

(I)

wherein:

R$^1$ is hydrogen; C$_{6-14}$aryl; or heteroaryl, optionally substituted with one or more substituents selected from the group consisting of C$_{1-6}$ alkoxy, nitro, halogen, amino, hydroxy, carboxy and esters thereof, carboxyalkyl, —CONHR$^6$, and —CONR$^6$R$^7$, wherein R$^6$ and R$^7$, which may be the same or different, are independently selected from C$_{1-8}$ alkyl, C$_{1-8}$ alkylaryl or C$_{6-14}$ aryl;

R$^2$ and R$^3$ are independently selected from C$_{1-8}$ alkyl, C$_{3-8}$ cycloalkyl, C$_{2-8}$ alkenyl, C$_{5-8}$cycloalkenyl, C$_{6-14}$ aryl, or aralkyl wherein each C$_{1-8}$ alkyl, C$_{3-8}$ cycloalkyl, C$_{2-8}$ alkenyl, C$_{5-8}$ cycloalkenyl, C$_{6-14}$ aryl, or aralkyl may be optionally substituted with one or more substituents selected from the group consisting of C$_{1-8}$ alkyl, halo, hydroxy, alkoxy, amino, aminoalkyl, —SH, heterocycle, carboxy and esters thereof, carboxyalkyl, —CONHR$^6$, and —CONR$^6$R$^7$, wherein R$^6$ and R$^7$, which may be the same or different, are independently selected from C$_{1-8}$ alkyl, C$_{1-8}$ alkylaryl or C$_{6-14}$ aryl; or R$^2$ and R$^3$ can together with the C atom to which these are attached form a 3 to 8-membered ring, wherin the ring members are C atoms;

R$^4$ is —OR$^8$, —NR$^8$R$^9$ or —SR$^8$, where R$^8$ and R$^9$, which may be the same or different, are independently selected from hydrogen; or C$_{1-8}$ alkyl, C$_{3-8}$ cycloalkyl, C$_{2-8}$ alkenyl, C$_{5-8}$ cycloalkenyl, aralkyl, heteroaryl, or C$_{6-14}$ aryl wherein each C$_{1-8}$ alkyl, C$_{3-8}$ cycloalkyl, C$_{2-8}$ alkenyl, C$_{5-8}$ cycloalkenyl, aralkyl, heteroaryl, or C$_{6-14}$ aryl may be optionally substituted with one or more substituents selected from the group consisting of halo, hydroxy, alkoxy, amino, aminoalkyl, —SH, carboxy and esters thereof, carboxyalkyl, —CONHR$^6$, and —CONR$^6$R$^7$, wherein R$^6$ and R$^7$, which may be the same or different, are independently selected from C$_{1-8}$ alkyl, C$_{1-8}$ alkylaryl or C$_{6-14}$ aryl;

R$^5$ is hydrogen; C$_{1-8}$ alkyl; or C$_{6-14}$ aryl; or R$^2$ and R$^5$ may together with the C atom and the N atom to which these are respectively attached form a 5- or 6-membered ring wherein the ring members contributed by R$^2$/R$^5$ are C atoms or R$^3$ and R$^5$ may together with the C atom and N atom to which these are respectively attached form a 5- or 6-membered ring wherein the ring members contributed by R$^2$/R$^5$ are C atoms;

or a pharmaceutically acceptable salt, ester or salt of an ester of the compound of formula (I).

2. A compound of formula (II)

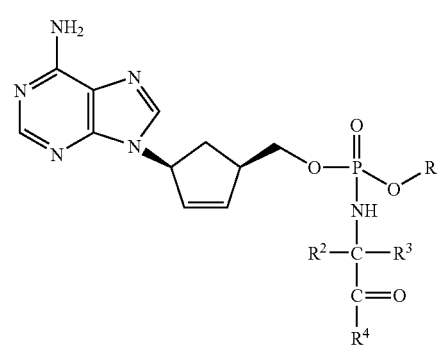

(II)

wherein:

R$^1$ is hydrogen; C$_{6-14}$ aryl; or heteroaryl, optionally substituted with one or more substituents selected from C$_{1-6}$ alkoxy, nitro, halogen, amino, carboxy and hydroxy, R$^2$ and R$^3$ are independently selected from hydrogen, C$_{1-6}$ alkyl, C$_{3-8}$ cycloalkyl, C$_{6-14}$ aryl, or aralkyl;

R$^4$ is OR$^{10}$, NHR$^{10}$ or SR$^{10}$, where R$^{10}$ is hydrogen, C$_{1-6}$ alkyl, C$_{3-8}$ cycloalkyl, or aralkyl; or NHR$^{11}$ wherein R$^{11}$ is C$_{1-6}$ alkyl, aralkyl, or C$_{6-14}$ aryl; or a pharmaceutically acceptable salt, ester or salt of an ester of the compound of formula (II).

3. A compound of formula (II) according to claim 2 wherein R$^1$ is H or C$_{6-14}$ aryl, R$^2$ is C$_{1-6}$ alkyl or aralkyl, R$^3$ is hydrogen, C$_{1-6}$ alkyl or aralkyl and R$^4$ is OR$^{10}$ wherein R$^{10}$ is C$_{1-6}$ alkyl or C$_{3-8}$ cycloalkyl.

4. A compound of formula (II) according to claim 2 wherein $R^1$ is $C_{6-14}$ aryl, $R^2$ is methyl, $R^3$ is hydrogen, and $R^4$ is $OR^{10}$ where $R^{10}$ is methyl or ethyl.

5. A compound of formula (II) according to claim 2 wherein $R^1$ is hydrogen.

6. A compound of formula (II) according to claim 2 wherein $R^1$ is $C_{6-14}$ aryl.

7. A compound of formula (I) according to claim 1 wherein wherein $R^2$ and $R^3$ are not both hydrogen.

8. A compound of formula (II) according to claim 2, wherein $R^1$ is Ph, $R^2$ is H, $R^3$ is Me and $R^4$ is OEt, or a pharmaceutically acceptable salt, ester or salt of an ester thereof.

9. A compound of formula I according to claim 1 selected from the group consisting of compounds wherein $R^1$, $R^2$, $R^3$, $R^4$ and $R^5$ are the moieties set out, respectively, in each line of the following table, where Me is methyl:

| $R^1$ | $R^2$ | $R^3$ | $R^4$ | $R^5$ |
|---|---|---|---|---|
| Ph | H | Me | OMe | H |
| Ph | H | Me | OEt | H |
| Ph | Me | H | OMe | H |
| Ph | H | Me | OCH$_2$Ph | H |
| Ph | H | CH$_2$Ph | OMe | H |
| Ph | H | CH$_2$Ph | OEt | H |
| H | H | CH$_2$Ph | OH | H |
| Ph | Me | Me | OMe | H |
| Ph | H | CH$_2$Ph(4-O-t-Bu) | OMe | H |
| Ph | H | Me | O-i-Pr | H |
| Ph | H | Me | O-t-Bu | H |
| Ph | H | Me | OCH$_2$-t-Bu | H |
| Ph | H | Me | OCH$_2$-cyclopropyl 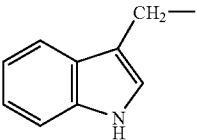 | H |
| Ph | H | CH$_2$CHMe$_2$ | OMe | H |
| Ph | H | CH$_2$Ph(4-OMe) | OMe | H |
| Ph | CH$_2$Ph | H | OMe | H |
| Ph | CH$_2$CHMe$_2$ | H | OMe | H |
| Ph | CH$_2$-(indol-3-yl) 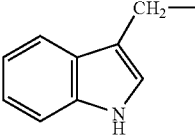 | H | OMe | H |
| Ph | CH$_2$-(indol-3-yl) | H | OMe | H |
| Ph | CHMe$_2$ | H | OMe | H |
| Ph | CH$_2$CO$_2$Me | H | OMe | H |
| Ph | H | $R^3/R^5$ = (CH$_2$)$_3$ | OMe | — |
| Ph | H | CH(Me)Et | OMe | H |
| Ph | H | n-Pr | OMe | H |
| Ph | H | CH$_2$Ph | O-i-Pr | H |
| Ph | H | CH$_2$Ph | O-t-Bu | H |
| Ph | H | CH$_2$Ph | OCH$_2$-t-Bu | H |
| Ph | H | CH$_2$Ph | OCH$_2$Ph | H |
| (2-MeO$_2$C)Ph | H | Me | OMe | H |
| (4-PhCOCH=CH)Ph | H | Me | OMe | H |
| Ph | H | H | OMe | H |
| Ph | H | i-Pr | OMe | H |
| Ph | H | CH$_2$CH$_2$SMe | OMe | H |
| Ph | Me | Me | OEt | H |
| Ph | Me | Me | O-i-Pr | H |
| Ph | Me | Me | OCH$_2$-t-Bu | H |
| Ph | — | $R^3/R^5$ = (CH$_2$)$_4$ | OMe | H |
| Ph | — | $R^3/R^5$ = (CH$_2$)$_5$ | OMe | H |
| Ph | H | CH$_2$CO$_2$Me | OMe | H |
| (4-Cl)Ph | H | Me | OMe | H |
| H | Me | H | NHMe | H | and pharmaceutically acceptable salt, ester or salt of an ester thereof.

10. A compound as claimed in claim 9 selected from the group consisting of compounds wherein $R^1$, $R^2$, $R^3$, $R^4$ and $R^5$ are the moieties set out, respectively, in each line of the following table, where Me is methyl:

| $R^1$ | $R^2$ | $R^3$ | $R^4$ | $R^5$ |
|---|---|---|---|---|
| Ph | H | Me | OMe | H |
| Ph | H | Me | OEt | H |
| Ph | Me | H | OMe | H |
| Ph | H | Me | OCH$_2$Ph | H |
| Ph | H | CH$_2$Ph | OMe | H |
| Ph | H | CH$_2$Ph | OEt | H |
| H | H | CH$_2$Ph | OH | H |
| Ph | Me | Me | OMe | H | and pharmaceutically acceptable salt, ester or salt of an ester thereof.

11. A compound according to claim 1 in the form of a single diastereomer with respect to the absolute configuration at phosphorus.

12. A compound according to claim 1 in the form of a mixture of diastereomers.

13. A method of treating Human Immunodeficiency Virus or hepatitis B virus infection in a human comprising administering to said human an effective anti-virus treatment amount of a compound of formula (I) or (II) according to claims 1 or 2 respectively, or a pharmaceutically acceptable salt, ester or salt of an ester thereof.

14. A method of treating a hepatitis B virus infection in a human comprising administering to said human an effective anti-hepatitis B treatment amount of a compound of formula I according to claim 1 wherein $R^1$ is Ph, $R^2$ is H, $R^3$ is Me, $R^4$ is OEt and $R^5$ is H or a compound of formula I according to claim 1 wherein $R^1$ is Ph, $R^2$ is H, $R^3$ is CH$_2$Ph, $R^4$ is OEt and $R^5$ is H, or a pharmaceutically acceptable salt, ester or salt of an ester thereof.

15. A compound according to claim 1 in the form of pharmaceutically acceptable salt.

16. A pharmaceutical composition comprising an effective anti-viral amount of a compound of formula (I) or (II) according to claims 1 or 2 respectively, or a pharmaceutically acceptable salt, ester or salt of an ester thereof together with a pharmaceutically acceptable carrier therefor.

17. The pharmaceutical composition according to claim 16, further comprising an antiviral agent other than a compound of formula (I) or (II) according to claims 1 and 2 respectively.

18. A pharmaceutical composition according to claim 16 in the form of a tablet or capsule.

19. A pharmaceutical composition according to claim 16 in the form of a solution, suspension, or syrup.

20. A patient pack comprising at least one active ingredient selected from a compound of formula (I) or (II) according to claims 1 or 2 respectively; and an information insert containing directions on the use of the compound.

21. A process for the preparation of a compound of formula (I) as defined in claim 1, said process comprising the reaction of a compound of formula (IV)

(IV)

with a compound of formula (VI)

(VI)

wherein $R^1$–$R^5$ are as hereinbefore defined for formula (I).

22. A process as claimed in claim 21 wherein the reaction is carried out in pyridine, pyridine-tetrahydrofuran or acetonitrile in the presence of t-butyl magnesium chloride.

23. A process for the preparation of a compound of formula (II) as defined in claim 2, said process comprising the reaction of a compound of formula (IV)

(IV)

with a compound of formula (V)

(V)

wherein $R^1$–$R^4$ are as hereinbefore defined for formula (II).

24. A process as claimed in claim 23 wherein the reaction is carried out in pyridine, pyridine-tetrahydrofuran or acetonitrile in the presence of t-butyl magnesium chloride.

25. A process as claimed in claim 21 wherein the compound obtained is in the form of a single isomer, a mixture of diastereomers, or a salt.

26. A method of treating Human Immunodeficiency Virus or hepatitis B virus infection in a human comprising administering to said human an effective amount of a compound according to claim 1.

* * * * *